(12) United States Patent
Kulagowski

(10) Patent No.: US 6,372,754 B1
(45) Date of Patent: Apr. 16, 2002

(54) SPIROCYCLIC KETONES AND THEIR USE AS TACHYKININ ANTAGONISTS

(75) Inventor: Janusz Jozef Kulagowski, Sawbridgeworth (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/913,059

(22) PCT Filed: Feb. 8, 2000

(86) PCT No.: PCT/GB00/00379

§ 371 Date: Aug. 8, 2001

§ 102(e) Date: Aug. 8, 2001

(87) PCT Pub. No.: WO00/47562

PCT Pub. Date: Aug. 17, 2000

(30) Foreign Application Priority Data

Feb. 9, 1999 (GB) .......................................... 99028813

(51) Int. Cl.⁷ ..................... A61K 31/438; C07D 221/20

(52) U.S. Cl. .......................................... 514/278; 546/16

(58) Field of Search ............................. 514/278; 546/16

(56) References Cited

FOREIGN PATENT DOCUMENTS

| WO | WO 94 03445 | 2/1994 |
|---|---|---|
| WO | WO 94 20500 | 9/1994 |
| WO | WO 97 49710 | 12/1997 |

*Primary Examiner*—Charandit S. Aulakh
(74) *Attorney, Agent, or Firm*—J. Eric Thies; David L. Rose

(57) ABSTRACT

The present invention relates compounds of the formula (I):

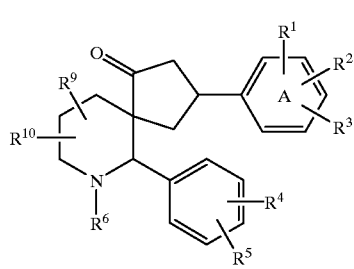

(I)

wherein $R^1$, $R^2$, $R^3$, $R^4$ and $R^5$ represent a variety of substituents;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}alkylR^{12}$, $CONR^{13}C_{2-6}alkenyl$, $CONR^{13}C_{2-6}alkynyl$, $COCONR^aR^b$, $CONR^aC(NR^b)NR^aR^b$, $CONR^a$heteroaryl, and phenyl optionally substituted by one, two or three substituents selected from $C_{1-6}$alky, $C_{1-6}$alkoxy, halogen and trifluoromethyl); or $R^6$ represents a group of formula —$CH_2C\equiv CCH_2NR^7R^8$ where $R^7$ and $R^8$ are as defined below; or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$;

or a pharmaceutical acceptable salt thereof.

The compounds are tachykinin antagonists and are of particular use in the treatment or prevention of depression, anxiety, pain, inflammation, migraine, emesis or postherpic neuralgia.

17 Claims, No Drawings

SPIROCYCLIC KETONES AND THEIR USE AS TACHYKININ ANTAGONISTS

CROSS REFERENCE TO RELATED APPLICATIONS

This application is a U.S. National Phase application under 35 U.S.C. § 371 of PCT Application No. PCT/GB00/00379, filed Feb. 8, 2000 now WO 00/47562, which claims priority under 35 U.S.C. § 119 from GB Application No. 9902881.3, filed Feb. 9, 1999.

This invention relates to a class of spirocyclic ketone compounds which are useful as tachykinin antagonists. More particularly, the compounds of the invention are 3-spiro-cyclopentanone piperidine derivatives.

International (PCT) patent specification no. WO 97/49710 (published Dec. 31st, 1997) discloses spiro-piperidine derivatives as substance P antagonists. In particular, WO 97/49710 relates to spirocyclic piperidine derivatives containing a 1-oxa-7-aza-spiro[4.5]decane core.

We have now found a further class of non-peptides which are potent antagonists of tachykinins, especially of the neurokinin-1 (substance P) receptor.

The present invention provides compounds of the formula (I):

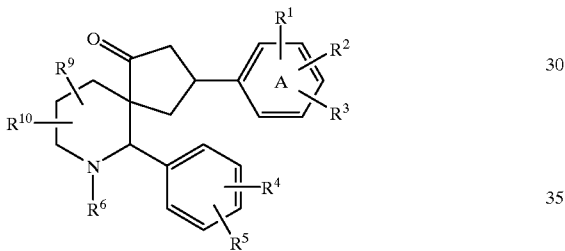

(I)

wherein
R$^1$ represents hydroxy, C$_{1-6}$alkyl, fluoroC$_{1-6}$alkyl, C$_{2-6}$alkenyl, C$_{3-7}$cycloalkyl, C$_{3-7}$cycloalkylC$_{1-4}$alkyl, C$_{1-6}$alkoxy, fluoroC$_{1-6}$alkoxy, C$_{1-6}$alkoxyC$_{1-4}$alkyl, C$_{1-6}$aralkoxyC$_{1-4}$alkoxy, fluoroC$_{1-6}$alkoxyC$_{1-4}$alkyl, C$_{2-6}$alkenyloxy, C$_{3-7}$cycloalkoxy, C$_{3-7}$cycloalkylC$_{1-4}$alkoxy, phenoxy, cyano, halogen, NR$^a$R$^b$, SR$^a$, SOR$^a$, SO$_2$R$^a$, OSO$_2$R$^a$, NR$^a$COR$^{14}$, COR$^a$, CO$_2$R$^a$ or CONR$^a$R$^b$ where R$^a$ and R$^b$ each independently represent hydrogen, C$_{1-4}$alkyl or fluoroC$_{1-4}$alkyl;

R$^2$ represents hydrogen, halogen, C$_{1-6}$alkyl or C$_{1-6}$alkoxy;

or when R$^2$ is adjacent to R$^1$, they may be joined together such that there is formed a 5- or 6-membered saturated or unsaturated ring containing one or two atoms selected from nitrogen, oxygen and sulphur, which ring is optionally substituted by a group selected from C$_{1-4}$alkyl, CF$_3$, =O or =S;

R$^3$ represents hydrogen, halogen, C$_{1-6}$alkyl, fluoroC$_{1-6}$alkyl, C$_{1-6}$alkoxy, fluoroC$_{1-6}$alkoxy, C$_{3-7}$cycloalkyl, C$_{3-7}$cycloalkylC$_{1-4}$alkyl, cyano, SR$^a$, SOR$^a$, SO$_2$R$^a$, NR$^a$R$^b$, NR$^a$COR$^{14}$, COR$^a$, CO$_2$R$^a$, CONR$^a$R$^b$ or C$_{1-4}$alkyl substituted by cyano, CO$_2$R$^a$ or CONR$^a$R$^b$ where R$^a$ and R$^b$ are as previously defined;

or R$^3$ represents a 5- or 6-membered aromatic heterocyclic group containing 1, 2, 3 or 4 heteroatoms, selected from nitrogen, oxygen and sulphur, which group is optionally substituted by one or two groups selected from C$_{1-6}$alkyl, C$_{1-6}$alkoxy, C$_{3-7}$cycloalkyl, C$_{3-7}$cycloalkylC$_{1-4}$alkyl, trifluoromethyl, OCF$_3$, NO$_2$, CN, SR$^a$, SOR$^a$, SO$_2$R$^a$, COR$^a$, CO$_2$R$^a$, phenyl, —(CH$_2$)$_r$NR$^a$R$^b$, —(CH$_2$)$_r$NR$^a$COR$^b$, —(CH$_2$)$_r$CONR$^a$R$^b$, or CH$_2$C(O)R$^a$, where R$^a$ and R$^b$ are as previously defined and r is zero, 1 or 2;

R$^4$ represents hydrogen, halogen, C$_{1-6}$alkyl, C$_{1-6}$alkoxy, CF$_3$, OCF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ are as previously defined;

R$^5$ represents hydrogen, halogen, C$_{1-6}$alkyl, CF$_3$ or C$_{1-6}$alkoxy substituted by C$_{1-4}$alkoxy;

R$^6$ represents hydrogen, COR$^a$, CO$_2$R$^a$, COCONR$^a$R$^b$, COCO$_2$R$^a$, C$_{1-6}$alkyl optionally substituted by a group selected from (CO$_2$R$^a$, CONR$^a$R$^b$, hydroxy, CN, COR$^a$, NR$^a$R$^b$, C(NOH)NR$^a$R$^b$, CONHphenyl(C$_{1-4}$alkyl), COCO$_2$R$^a$, CONHNR$^a$R$^b$, C(S)NR$^a$R$^b$, CONR$^a$C$_{1-6}$alkylR$^{12}$, CONR$^{13}$C$_{2-6}$alkenyl, CONR$^{13}$C$_{2-6}$alkynyl, COCONR$^a$R$^b$, CONR$^a$C(NR$^b$)NR$^a$R$^b$, CONR$^a$heteroaryl, and phenyl optionally substituted by one, two or three substituents selected from C$_{1-6}$alkyl, C$_{1-6}$alkoxy, halogen and trifluoromethyl);

or R$^6$ represents a group of the formula —CH$_2$C≡CCH$_2$NR$^7$R$^8$ where R$^7$ and R$^8$ are as defined below;

or R$^6$ represents C$_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula ZNR$^7$R$^8$ where
Z is C$_{1-6}$alkylene or C$_{3-6}$cycloalkyl;
R$^7$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;
R$^8$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy, hydroxyl or a 4, 5 or 6 membered heteroaliphatic ring containing one or two heteroatoms selected from N, O and S;
or R$^7$, R$^8$ and the nitrogen atom to which they are attached form a heteroaliphatic ring of 4 to 7 ring atoms, optionally substituted by one or two groups selected from hydroxy or C$_{1-4}$alkoxy optionally substituted by a C$_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;
or R$^7$, R$^8$ and the nitrogen atom to which they are attached form a non-aromatic azabicyclic ring system of 6 to 12 ring atoms;
or Z, R$^7$ and the nitrogen atom to which they are attached form a heteroaliphatic ring to 4 to 7 ring atoms which may optionally contain an oxygen ring atom;

R$^9$ and R$^{10}$ each independently represent hydrogen, halogen, C$_{1-6}$alkyl, CH$_2$OR$^e$, oxo, CO$_2$R$^a$ or CONR$^a$R$^b$ where R$^a$ and R$^b$ are as previously defined and Re represents hydrogen, C$_{1-6}$alkyl or phenyl;
R$^{12}$ represents OR$^a$, CONR$^a$R$^b$ or heteroaryl;
R$^{13}$ represents hydrogen or C$_{1-6}$alkyl; and
R$^{14}$ represents C$_{1-6}$alkyl, C$_{1-6}$alkoxy, fluoroC$_{1-6}$alkyl or phenyl;

and pharmaceutically acceptable salts thereof.

According to a first aspect of the present invention, phenyl ring A is preferably a 2,5-disubstituted phenyl ring.

According to a second alternative aspect of the present invention, phenyl ring A is preferably a 3,5-disubstituted phenyl ring.

A preferred class of compound of formula (I) is that wherein $R^1$ is hydroxy, $C_{1-6}$alkyl, fluoro$C_{1-6}$alkyl, $C_{2-6}$alkenyl, $C_{1-6}$alkoxy, fluoro$C_{1-6}$alkoxy, $C_{2-6}$alkeny oxy, $C_{3-7}$cycloalkoxy, $C_{3-7}$cycloalkyl$C_{1-4}$alkoxy, cyano, $NR^aR^b$, $SR^a$, $OSO_2R^a$, or $R^1$ together with the group $R^2$ form a 5-membered saturated ring containing one oxygen atom.

A particularly preferred class of compound of formula (I) is that wherein $R^1$ is $C_{1-6}$alkyl, fluoro$C_{1-6}$alkyl, $C_{1-6}$alkoxy, fluoro$C_{1-6}$alkoxy, $C_{3-7}$cycloalkoxy or $C_{3-7}$cycloalkoxy$C_{1-4}$alkyl, especially methyl, trifluoromethyl, methoxy, trifluoromethoxy, 2,2,2-trifluoroethoxy, difluoromethoxy, cyclopropoxy or cyclopropylmethoxy.

Another preferred class of compound of formula (I) is that wherein $R^2$ is a hydrogen, fluorine or chlorine atom, especially a hydrogen atom.

A further preferred class of compound of formula (I) is that wherein $R^3$ is hydrogen, halogen, fluoro$C_{1-6}$alkyl, fluoro$C_{1-6}$alkoxy, cyano, $NR^aR^b$, $NR^aCOR^{14}$ (where $R^{14}$ is preferably methyl, methoxy, trifluoromethyl or phenyl), or a 5-membered aromatic heterocyclic group as previously defined.

Also preferred is the class of compound of formula (I) in which $R^3$ is $C_{1-6}$alkyl, fluoro$C_{1-6}$alkyl, fluoro$C_{1-6}$alkoxy or a 5-membered aromatic heterocyclic group as previously defined, especially methyl, trifluoromethyl, trifluoromethoxy or 5-trifluoromethyl-1,2,3,4-tetrazol-1-yl.

Certain particularly apt compounds of the present invention include those wherein $R^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein $R^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each heteroaryl group being optionally substituted as previously defined.

Particularly preferred compounds of the present invention are those wherein $R^3$ is a group selected from furan, pyridine, pyrimidine, 1,2,3-triazole, 1,2,4-triazole and tetrazole, each heteroaryl group being optionally substituted as previously defined.

An especially preferred class of compound of formula (I) is that wherein $R^3$ is the group

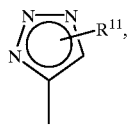

where $R^{11}$ is hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $COR^a$, $CO_2R^a$, $(CH_2)_rCONR^aR^b$, $(CH_2)_rNR^aR^b$ or $(CH_2)_rNR^aCOR^b$, where $R^a$ and $R^b$ are hydrogen or $C_{1-4}$alkyl, and r is zero, 1 or 2.

Another especially preferred class of compound of formula (I) is that wherein $R^3$ is the group

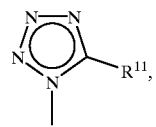

wherein $R^{11}$ is as previously defined.

Another especially preferred class of compound of formula (I) is that wherein $R^3$ is the group

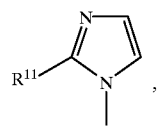

wherein $R^{11}$ is as previously defined.

$R^{11}$ is preferably hydrogen, $C_{1-4}$alkyl, especially methyl, $CF_3$, $(CH_2)_rCONR^aR^b$, $SOR^a$ or $SO_2R^a$ where $R^a$, $R^b$ and r are as previously defined. Most especially, $R^{11}$ is $CF_3$.

A further preferred class of compound of formula (I) is that wherein $R^4$ is a hydrogen atom or a fluorine atom.

Another preferred class of compound of formula (I) is that in which $R^5$ is a hydrogen atom.

A further preferred class of compound of formula (I) is that wherein $R^6$ is a $C_{1-6}$alkyl group, in particular $CH_2$, $CH(CH_3)$ and $CH_2CH_2$ and especially $CH_2$, substituted by a 5-membered heterocyclic ring containing 2 or 3 nitrogen atoms as previously defined.

In particular, the 5-membered ring is a heterocyclic ring selected from:

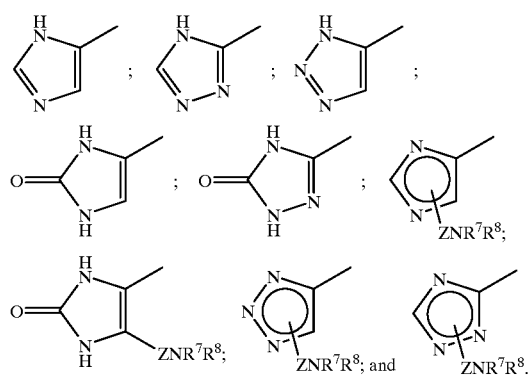

A particularly preferred heterocyclic ring is:

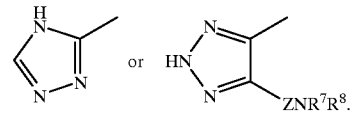

Another preferred class of compound of formula (I) is that wherein one of $R^9$ and $R^{10}$ is hydrogen, and especially wherein $R^9$ and $R^{10}$ are both hydrogen atoms.

One favoured group of compounds of the present invention are of the formula (Ia) and pharmaceutically acceptable salts thereof:

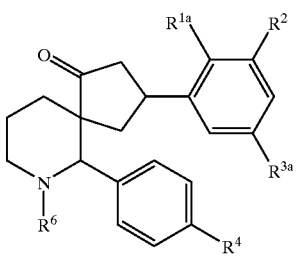

(Ia)

wherein $R^2$, $R^4$ and $R^6$ are as defined in relation to formula (I);

$R^{1a}$ is $C_{1-4}$alkoxy, fluoro$C_{1-4}$alkoxy, $C_{3-5}$cycloalkoxy or $C_{3-5}$cycloalkoxy$C_{1-2}$alkyl; and $R^{3a}$ is fluoro$C_{1-4}$alkoxy.

$R^{1a}$ is preferably methoxy, trifluoromethoxy, 2,2,2-trifluoroethoxy, difluoromethoxy, cyclopropoxy or cyclopropylmethoxy.

$R^{3a}$ is preferably trifluoromethoxy.

Another favoured group of compounds of the present invention are of the formula (Ib) and pharmaceutically acceptable salts thereof:

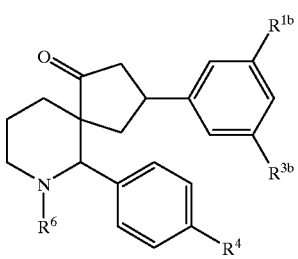

(Ib)

wherein $R^4$ and $R^6$ are as defined in relation to formula (I);

$R^{1b}$ is $C_{1-4}$alkyl, or fluoro$C_{1-4}$alkyl; and $R^{3b}$ is $C_{1-4}$alkyl or fluoro$C_{1-4}$alkyl.

$R^{1b}$ is preferably methyl or trifluoromethyl. Most especially $R^{1b}$ is trifluoromethyl.

$R^{3b}$ is preferably methyl or trifluoromethyl. Most especially $R^{3b}$ is trifluoromethyl.

Most preferably, $R^{1b}$ and $R^{3b}$ are the same.

With respect to compounds of the formula (I), Z (where present), may be a linear, branched or cyclic group. Favourably Z contains 1 to 4 carbon atoms and most favourably 1 or 2 carbon atoms. A particularly favourable group Z is $CH_2$.

With respect to compounds of the formula (I), $R^7$ may aptly be a $C_{1-4}$alkyl group or a $C_{2-4}$alkyl group substituted by a hydroxyl or $C_{1-2}$alkoxy group, $R^8$ may aptly be a $C_{1-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

Particularly suitable moieties $ZNR^7R^8$ include those wherein Z is $CH_2$ or $CH_2CH_2$ and $NR^7R^8$ is amino, methylamino, dimethylamino, diethylamino, azetidinyl, pyrrolidino and morpholino.

In particular, Z is preferably $CH_2$ and $NR^7R^8$ is preferably dimethylamino, azetidinyl or pyrrolidino, especially dimethylamino.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and fluoro$C_{1-6}$alkoxy" means a $C_{1-6}$alkyl or $C_{1-6}$alkoxy group in which one or more (in particular, 1 to 3) hydrogen atoms have been replaced by fluorine atoms. Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "heteroaryl" as a group or part of a group means a 5- or 6-membered heteroaromatic ring containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, and tetrazolyl.

When used herein the term "halogen" means fluorine, chlorine, bromine and iodine. The most apt halogens are fluorine and chlorine of which fluorine is preferred, unless otherwise stated.

Specific compounds within the scope of this invention include:

(3RS,5RS,6SR)-3-(2-methoxy-5-trifluoromethoxy)phenyl-6-phenyl-7H-azaspiro[4.5]decan-1-one;

(3RS,5RS,6SR)-3-(2-methoxy-5-trifluoromethoxy)phenyl-6-phenyl-7-(1,2,4-triazol-3-yl)methyl-7-azaspiro[4.5]decan-1-one;
(3RS,5RS,6SR)-3-(2-cyclopropoxy-5-trifluoromethoxy)phenyl-6-phenyl-7-azaspiro[4.5]decan-1-one;
(3SR,5RS,6SR)-3-(2-cyclopropoxy-5-trifluoromethoxy)phenyl-6-phenyl-7-azaspiro[4.5]decan-1-one;
(3RS,5RS,6SR)-3-(2-cyclopropoxyoxy-5-trifluoromethoxy)phenyl-6-phenyl-7-(1,2,4-triazol-3-yl)methyl-7-azaspiro[4.5]decan-1-one;
(3SR,5RS,6SR)-3-(2-methoxy-5-trifluoromethoxy)phenyl-6-phenyl-7H-azaspiro[4.5]decan-1-one;
(3RS,5RS,6SR)-3-(2-isopropoxy-5-trifluoromethoxy)phenyl-6-phenyl-7-azaspiro[4,5]decan-1-one;
(3RS,5RS,6SR)-3-(2-isopropoxy-5-trifluoromethoxy)phenyl-6-phenyl-7-(1,2,4-triazol-3-yl)methyl-7-azaspiro[4,5]decan-1-one;
(3RS,5RS,6SR)-3-(2-hydroxy-5-trifluoromethoxy)phenyl-6-phenyl-7-azaspiro[4,5,]decan-1-one;
(3RS,5RS,6SR)-3-(2-cyclopropylmethyloxy-5-trifluoromethoxy)phenyl-6-phenyl-7-azaspiro[4,5,]decan-1-one;
(3RS,5RS,6SR)-3-(2-difluoromethoxy-5-trifluoromethoxy)phenyl-6-phenyl-7-azaspiro[4,5]decan-1-one;
(3RS,5RS,6SR)-3-(2-difluoromethoxy-5-trifluoromethoxy)phenyl-6-phenyl-7-(1,2,4-triazol-3-yl)methyl-7-azaspiro[4,5]decan-1-one;
(3RS,5RS,6SR)-6-phenyl-3-(2-(2,2,2-trifluoroethoxy-5-trifluoromethoxy)phenyl-7-azaspiro[4,5,]decan-1-one;
(3RS,5RS,6SR)-6-phenyl-7-(1,2,4-triazol-3-yl)methyl-3-(2-(2,2,2-trifluoroethoxy-5-trifluoromethoxy)phenyl-7-azaspiro[4,5]decan-1-one;
(3SR,5RS,6SR)-3-(3,5-dimethyl)phenyl-6-phenyl-7-azaspiro[4,5]decan-1-one;
(3SR,5RS,6SR)-3-(3,5-dimethyl)phenyl-6-phenyl-7-(1,2,4-triazol-3-yl)methyl-7-azaspiro[4,5]decan-1-one;
(3RS,5RS,6SR)-3-(3,5-bis(trifluoromethyl))phenyl-6-phenyl-7-azaspiro[4,5]decan-1-one;
(3RS,5RS,6SR)-3-(3,5-bis(trifluoromethyl))phenyl-6-phenyl-7-(1,2,4-triazol-3-yl)methyl-7-azaspiro[4,5]decan-1-one;
(3SR,5RS,6SR)-3-(2-difluoromethoxy-5-trifluoromethoxy)phenyl-6-phenyl-7-azaspiro[4,5]decan-1-one;
(3SR,5RS,6SR)-3-(2-difluoromethoxy-5-trifluoromethoxy)phenyl-6-phenyl-7-(1,2,4-triazol-3-yl)methyl-7-azaspiro[4,5]decan-1-one;
(3RS,5RS,6SR)-3-(2-difluoromethoxy-5-(5-(trifluoromethyl)tetrazolyl))phenyl-6-phenyl-7-azaspiro[4,5]decan-1-one;
(3SR,5RS,6SR)-3-(2-difluoromethoxy-5-(5-trifluoromethyl)tetrazolyl)phenyl-6-phenyl-7-azaspiro[4,5]decan-1-one;
(3RS,5RS,6SR)-3-(2,6-dimethyl)phenyl-6-phenyl-7-azaspiro[4,5]decan-1-one;
and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (1) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I), (Ia) and (Ib) will have the stereochemistry of the 5- and 6-positions that is possessed by the compound of Example 1 (i.e. 5-(R) and 6-(S)). Thus for example as shown in formula (Ic)

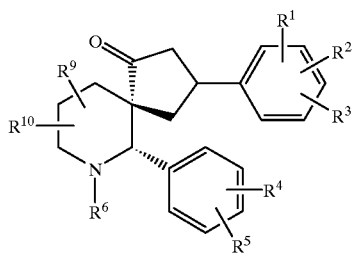

(Ic)

It will be appreciated that the preferred definitions of the various substituents recited herein may be taken alone or in combination and, unless otherwise stated, apply to the generic formula for compounds of the present invention as well as to the preferred classes of compound represented by formula (Ia), formula (Ib) and formula (Ic).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or domperidone or GABA$_B$ receptor agonists such as baclofen. Additionally, a compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Suitable methods for determining the anti-emetic effects of compounds of the present invention are well known in the art, for example, using the ferret model of cisplatin-induced emesis described by F. D. Tattersall et al, in *Eur. J. Pharmacol.,* (1993) 250, R5–R6.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache, including migraine, acute or chronic tension headache, cluster headache, temporomandibular pain, and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination.

Thus, for example, for the treatment of respiratory diseases such as asthma, a compound of formula (I) may be used in conjunction with a bronchodilator, such as a β$_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification nos. 0 480 717 and 0 604 114 and in U.S. Pat. Nos. 4,859,692 and 5,270, 324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-$HT_{1A}$ agonists or antagonists, especially 5-$HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-$HT_{1A}$ receptor agonists or antagonists include, in particular, the 5-$HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

Suitable anoretic agents of use in combination with a compound of the present invention include, but are not limited to, aminorex, amphechoral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptble salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared (kg/m$^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

A further aspect of the present invention comprises the use of a compound of formula (I) for achieving a chronobiologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

The present invention is further directed to the use of a compound of formula (I) or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of formula (I) or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

As used herein the term "mammals" includes animals of economic importance such as bovine, ovine, and porcine animals, especially those that produce meat, as well as domestic animals, sports animals, zoo animals, and humans, the latter being preferred.

It will be appreciated that when using any combination described herein, both the compound of formula (I) and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I) may be prepared by the reaction of a compound of formula (II)

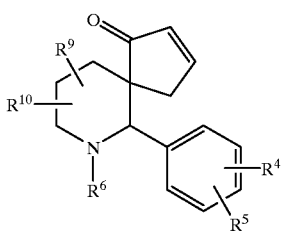

(II)

wherein $R^4$, $R^5$, $R^6$, $R^9$ and $R^{10}$ are as defined in relation to formula (I), with a Grignard reagent of the formula (III)

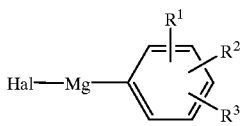

(III)

wherein $R^1$, $R^2$ and $R^3$ are as defined in relation to formula (I) and Hal is a halogen atom, preferably bromine or chlorine. The reaction is preferably effected in the presence of a copper ion catalyst to increase 1,4 addition at the double bond. Suitable copper ion catalysts include copper(I)iodide, copper(I)chloride and copper(II)acetate.

Formation of the Grignard reagent of formula (III) is conveniently effected in situ by the reaction of the corresponding aryl halide with magnesium in a suitable solvent such as an ether, for example, tetrahydrofuran.

According to another general process (B), compounds of formula (I) may be prepared by the reduction of a compound of formula (IV):

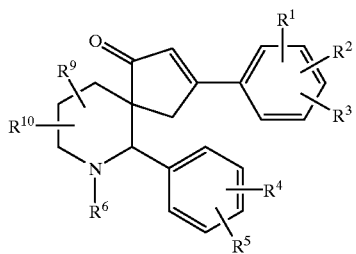

(IV)

wherein $R^1$, $R^2$, $R^3$, $R^4$, $R^5$, $R^6$, $R^9$ and $R^{10}$ are as defined in relation to formula (I).

Suitable reducing conditions whereby the double bond is selectively reduced without affecting the carbonyl group include: sodium borohydride with a transition metal salt catalyst; hydrogen and a rhodium catalyst; tributyltin hydride and tetrakis(triphenylphosphine)palladium (0); and tributyltin hydride with copper(I)iodide and lithium chloride.

The selection of reducing agent may also be used to preferentially prepare the 3-position epimers. In particular, dissolving metal reduction using, for example, magnesium in methanol, may be used to prepare the 3-β epimer.

According to another general process (C), compounds of formula (I) may be prepared by the interconversion of a corresponding compound of formula (I) in which $R^6$ is H, hereinafter referred to as formula (V)

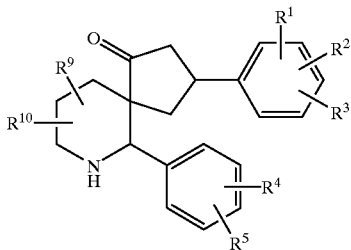

(V)

by reaction with a compound of formula (VI):

$$LG\text{—}R^{6a} \qquad (VI)$$

where $R^{6a}$ is a group of the formula $R^6$ as defined in relation to formula (I) (other than H) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

Suitable alternative methods for introducing the group $R^6$ are described, for instance, in International Patent Specification No. WO 95/18124.

According to another general process (D), compounds of formula (I) wherein $R^1$ is $C_{1-6}$alkoxy, fluoro$C_{1-6}$alkoxy, $C_{2-6}$alkenoxy, $C_{3-7}$cycloalkoxy, or $C_{3-7}$cycloalkyl$C_{1-4}$alkoxy, may be prepared by the interconversion of a compound of formula (I) wherein $R^1$ is hydroxy, hereinafter referred to as formula (VII)

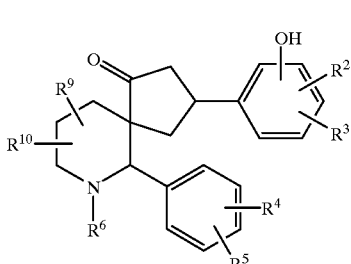

(VII)

by reaction with an appropriate alkyl-, fluoroalkyl-, alkenyl-, cycloalkyl-, or cycloalkylalkyl-halide, especially the iodide, in the presence of a base.

Suitable bases include alkali metal hydrides, such as sodium hydride, in a suitable solvent such as dimethylformamide. The reaction is conveniently effected at about room temperature.

The compounds of formula (VII) are particularly useful where specific 3-position epimers are required since the phenols are generally separable by chromatography.

According to another general process (E), compounds of formula (I) may be prepared from a compound of formula (II) and a compound of formula (IV), where Hal in the compound of formula (IV) is chlorine, bromine or, preferably, iodine, by a reductive Heck reaction using a palladium catalyst such as palladium acetate with, for example, tri-o-tolylphosphine, dimethylformamide and tributylamine, or tetrabutylammonium chloride and dimethylformamide, and a reducing agent, preferably formic acid or a salt thereof, such as potassium formate.

According to another general process (F), compounds of formula (I) wherein $R^1$ is cyclopropoxy may be prepared from a compound of formula (VIII):

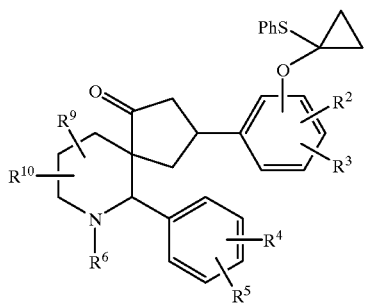

(VIII)

by reaction with lithium naphthalenide in tetrahydrofuran. The reaction is preferably effected at reduced temperature, for example at about −78° C.

According to another general process (G), compounds of formula (I) wherein $R^6$ is 1,2,4-triazol-3-ylmethyl, may be prepared from a compound of formula (V) and N-formyl-2-chloroacetamidhyrazone (Yangisawa, *J. Med. Chem.*, 1984, 27:849) in the presence of a base.

Suitable bases of use in the reaction include alkali metal carbonates such as potassium carbonate. The reaction is conveniently effected in an anhydrous organic solvent such as anhydrous dimethylformamide, preferably at elevated temperature such as 60° C. rising to between 100° C. and 140° C.

According to another general process (H), compounds of formula (I) wherein $R^6$ is a 1,2,3-triazol-4-ylmethyl group substituted by $CH_2NR^7R^8$, may be prepared by reaction of a compound of formula (IX)

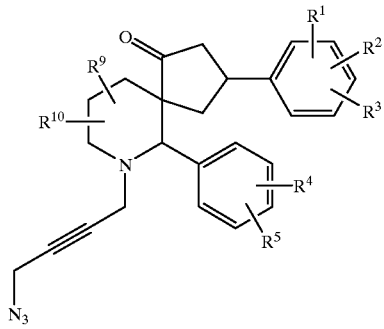

(IX)

with an amine of formula $NHR^7R^8$, in a suitable solvent such as an ether, for example, dioxan, at elevated temperature, for example, at the reflux temperature of the solvent.

Further details of suitable procedures will be found in the accompanying Examples.

Compounds of formula (II) may be prepared by heating a compound of formula (X)

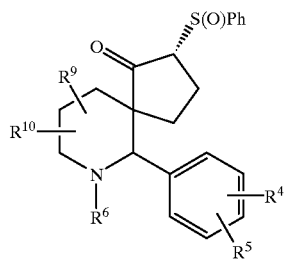

(X)

wherein Ph is a phenyl group, in the presence of an organic base, preferably pyridine. The reaction is conveniently effected at reflux.

Compounds of formula (X) may be prepared by the oxidation and subsequent cyclisation of a compound of formula (XI)

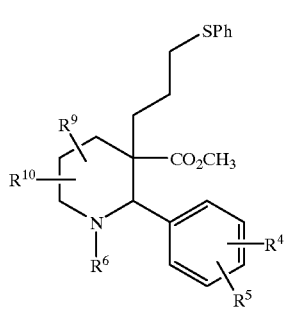

(XI)

Oxidation is effected under conventional conditions using, for example, sodium periodate in a suitable solvent such as an alcohol, for example, methanol, optionally including water. The intramolecular cyclisation is conveniently effected using, for example, lithium bis(trimethylsilyl) amide. The reaction is preferably effected in an ether, for example, tetrahydrofuran, at reduced temperature, for example at about −78°.

Compounds of formula (XI) may be prepared by the reaction of a compound of formula (XII)

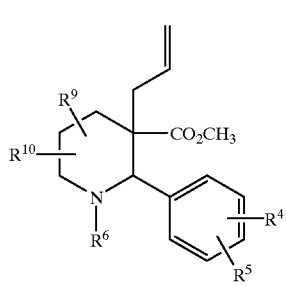

(XII)

with thiophenol in the presence of azaisobutyronitrile in a suitable solvent such as an aromatic hydrocarbon, for example toluene, conveniently at an elevated temperature, for example at about 80° C.

Compounds of formula (XII) may be prepared by the reaction of a compound of formula (XIII)

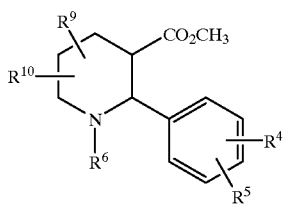

(XIII)

with allyl bromide. The condensation is conveniently effected in the presence of lithium bis(trimethylsilyl)amide. The reaction is preferably effected in an ether, for example, tetrahydrofuran, at reduced temperature, for example at about −78° C.

Compounds of formula (XIII) may be prepared stepwise from 2-chloronicotinoyl chloride. Firstly, the corresponding methyl ester is prepared by conventional esterification, for example, by reaction with methanol in pyridine. Then the appropriate 2-aryl moiety is introduced by reaction of an appropriately substituted phenyl-trialkyltin derivative with the 2-chloro nicotinic acid methyl ester in the presence of lithium chloride and a transition metal catalyst such as tetrakis(triphenylphosphine)palladium (0). Suitable solvents for this step include aromatic hydrocarbons, for example toluene.

The resulting 2-arylnicotinic acid methyl ester is then reduced to the corresponding 2-arylnipecotic acid methyl ester using, for example, catalytic hydrogenation in the presence of palladium hydroxide and hydrochloric acid. This step is conveniently effected in a solvent such as an alcohol, for example methanol. The resultant compound is then conveniently N-protected on the piperidine nitrogen using, for example, a tertiary-butoxycarbonyl protecting group, before subsequent use.

Compounds of formula (III) may be prepared from known compounds or from aryl halide derivatives prepared by methods described herein or otherwise well-known in the published literature.

Compounds of formula (IV) are useful intermediates for the steroselective preparation of compounds of formula (I). Compounds of formula (IV) may be prepared by the reaction of a corresponding compound of formula (I) with lithium dialuminium hydride in tetrahydrofuran, followed by treatment with a phenylselenyl halide (chloride or bromide) to give a phenylselenide derivative which is then treated with hydrogen peroxide to give the compound of formula (VI). The elimination is preferably effected at 0° C. rising to about room temperature. More preferably, benzeneseleninic anhydride may be used to afford the compound of formula (IV) in a single step.

Intermediates of formula (V) may be prepared, for example, in a similar manner to that descibed in general processes (A) and (B), preferably with an amino protecting group on the piperidine nitrogen in the compound of formulae (II) and (IV). Suitable amino protecting groups include alkoxycarbonyl groups such as tert-butoxycarbonyl and trichloroethoxycarbonyl, aralkyloxycarbonyl groups such as benzyloxycarbonyl, or aralkyl groups such as benzyl. Removal of the protecting group is effected by conventional procedures thus, for example, tert-butoxycarbonyl groups may be removed under acidic conditions using, for example, trifluoroacetic acid; tert-butoxycarbonyl groups, together with benzyloxycarbonyl and benzyl groups, may also be removed by hydrogenolysis in the presence of a catalyst, for example, palladium; and trichloroethoxycarbonyl groups may be removed with zinc dust.

Compounds of formula (VII) may be prepared from the appropriate phenolic precursor (or a protected (e.g. benzyloxy) derivative thereof) using, for example, the methods of processes (A), (B) or (C).

Compounds of formula (VIII) may be prepared from a compound of formula (VII) by reaction with (1-iodo-cycloprop-1-yl)phenylsulfide.

Compounds of formula (IX) may be prepared from a compound of formula (XIV)

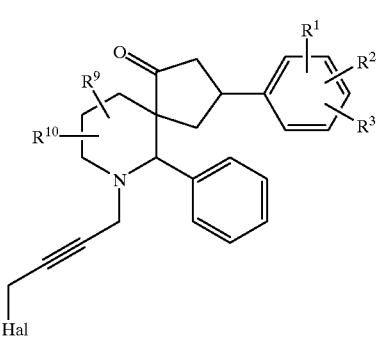

(XIV)

wherein Hal is a halogen atom, for example, chlorine, bromine or iodine, specially chlorine, by reaction with an azide, for example, sodium azide in a suitable solvent such as dimethylsulfoxide at or below room temperature.

Compounds of formula (XIV) may be prepared by a dropwise addition of a compound of formula (V) to a dihaloacetylene of formula Hal-$CH_2$—C≡C—$CH_2$-Hal where each Hal is independently chlorine, bromine or iodine, especially chlorine. The reaction is conveniently effected in a suitable solvent such as dimethylformamide in the presence of a base such as potassium carbonate.

It will be appreciated that compounds of the formula (I) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (IV) above may be prepared, for example, from the corresponding phenol derivative using, for example, the procedures described in the accompanying Examples, or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

For the avoidance of doubt, the nomenclature adhered to throughout this specification is based upon the following structures:

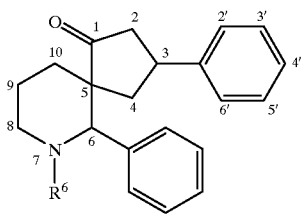

The following non-limiting Examples serve to illustrate the preparation of compounds of the present invention:

DESCRIPTION 1

Methyl 2-chloronicotinate

Methanol (5 ml, 0.12 mol) was added to a solution of 2-chloronicotinyl chloride (17.6 g, 0.1 mol) in pyridine (75 ml) and the mixture stirred for 2 hours before being filtered. The filtrate was evaporated and the residue partitioned between ethyl acetate (100 ml) and water (50 ml). The organic layer was washed sequentially with aqueous citric acid (10%; 50 ml), sodium carbonate (saturated; 50 ml), and brine (50 ml), dried over $MgSO_4$ and evaporated to leave the product as yellow oil (15.5 g, 90%). $^1H$ NMR (250 MHz, $CDCl_3$) δ 3.97 (3H, s), 7.34 (1H, dd, J 7.9, 4.9 Hz), 8.17 (1H, dd, J 7.9, 2.0 Hz), 8.51 (1H, dd, J 4.9, 2.0 Hz).

DESCRIPTION 2

Methyl 2-phenylnicotinate

A mixture of methyl 2-chloronicotinate (3.10 g, 18.1 mmol), phenyltributyltin (6.30 g, 17 mmol), lithium chloride (5.04 g, 120 mmol), and tetrakis(triphenylphosphine)palladium (1.12 g, 1 mmol) in toluene (65 ml) was degassed and then stirred under a nitrogen atmosphere overnight at 90° C. and at reflux for 5 hours. The cooled reaction mixture was filtered, the filtrate evaporated, and the residue partitioned between acetonitrile (50 ml) and hexane (5×20 ml). The combined hexane layers were extracted with hydrochloric acid (1M, 4×10 ml), the extracts washed with ethyl acetate (15 ml), and basified (4M NaOH). The resulting suspension was extracted with dichloromethane (4×10 ml), the combined extracts dried over $MgSO_4$ and evaporated to leave a colourless oil. Meanwhile, the acetonitrile layer from above was evaporated and the residual oil dissolved in diethyl ether (50 ml) and ethyl acetate (25 ml) and the solution extracted with hydrochloric acid (1M, 4×10 ml). Basification of the acid extracts (4M NaOH) and extraction of the resulting suspension with dichloromethane (4×10 ml) followed by drying of the combined extracts with $MgSO_4$ and evaporation gave an oil which was combined with that obtained as described above (2.62 g).

Drying ($MgSO_4$) of the ether-ethyl acetate layer from above followed by evaporation gave an oil, which was subjected to column chromatography over silica gel, eluting with 3:1 hexanes-ethyl acetate, to provide a further 0.33 g of the desired product. $^1H$ NMR (250 MHz, $CDCl_3$) δ 3.70 (3H, s), 7.34 (1H, dd, J 7.9, 4.9 Hz), 7.42–7.47 (3H, m), 7.53–7.57 (2H, m), 8.10 (1H, dd, J 7.9, 1.8 Hz), 8.78 (1H, dd, J 4.9, 1.8 Hz).

DESCRIPTION 3

(2RS,3RS) Methyl 2-phenylpiperidine-3-carboxylate

A mixture of methyl 2-phenylnicotinate (9.43 g, 44.3 mmol) and palladium on carbon (10%; 2.5 g) in methanol (150 ml) containing hydrochloric acid (5M, 25 ml) was shaken for 72 hours under an atmosphere of hydrogen at 50 psi. Palladium hydroxide on carbon (20%; 1.0 g) was then added and hydrogenation resumed for a further 24 hours. A further portion of palladium hydroxide on carbon (1.0 g) was added, and hydrogenation continued for 24 hours more, until thin layer chromatography indicated no more starting material to be present. The suspension was filtered and evaporated to dryness, leaving the desired product as the hydrochloride salt. A small portion of this was basified with sodium carbonate to liberate the free base, isolated as a colourless oil. $^1H$ NMR (360 MHz, $CDCl_3$) δ 1.47–1.53 (1H, m), 1.78–1.90 (2H, m), 1.91–1.99 (1H, m), 2.81 (1H, dt, J 12.4, 2.9 Hz), 2.96–2.99 (1H, m), 3.31–3.36 (1H, m) 3.43 (3H, s), 3.95 (1H, d, J 3.4 Hz), 7.18–7.32 (5H, m).

DESCRIPTION 4

(2RS,3RS) Methyl 1-tert-butyloxycarbonyl-2-phenylpiperidine-3-carboxylate

The product of Description 3 (44 mmol) was stirred overnight with di-tert-butyl dicarbonate (10.9 g, 50 mmol) in a mixture of dichloromethane (100 ml) and aqueous sodium carbonate (saturated, 100 ml). The mixture was diluted with water (100 ml), the layers separated, and N,N-dimethylethylenediamine (5 ml) added to the organic phase. After standing for 30 minutes, the solution was washed with aqueous citric acid (10%, 2×50 ml) and brine (50 ml), dried over $MgSO_4$ and evaporated to leave a gum which was purified by silica gel chromatography, using 4:1 hexanes-ethyl acetate as eluant to give the product as a viscous, colourless oil (11.44 g, 82%). $^1H$ NMR (360 MHz, $CDCl_3$) δ 1.46–1.58 (1H, m), 1.48 (9H, s), 1.71–1.81 (1H, m), 1.94–2.13 (2H, m), 2.61–2.77 (1H, m), 2.93 (1H, dt, J 12.4, 4.9 Hz), 3.60 (3H, s), 3.81–4.08 (1H, m), 5.71–6.07 (1H, m), 7.20–7.30 (5H, m).

DESCRIPTION 5

(2RS,3SR) Methyl 1-tert-butyloxycarbonyl-2-phenyl-3-(3-propenyl)piperidine-3-carboxylate To a stirred solution of the ester of Description 4 (2.10 g, 6.6 mmol) in THF (35 ml) at −78° C. was added a solution of lithium hexamethyldisilazide in THF (1M, 8 ml), followed after 1 hour by allyl bromide (0.97 g, 8 mmol). After a further 30 minutes at −78° C., the solution was allowed to warm to room temperature and stirred overnight, before being evaporated. The residue was partitioned between aqueous citric acid (5%, 40 ml) and ethyl acetate (3×20 ml), the combined organic layers washed with brine (20 ml), dried over $MgSO_4$, evaporated, and the residue chromatographed on silica gel, eluting with 15% ethyl acetate in hexanes, to afford the desired product as a colourless gum (2.18 g, 92%). $^{1H\ NMR}$ (360 MHz, $CDCl_3$) δ 1.50 (9H, s), 1.56–1.80 (1H, m), 1.95–2.03 (1H, m), 2.21–2.34 (1H, m), 2.58–2.76 (2H, m), 3.45 (3H, s), 3.90–4.07 (1H, m), 5.05–5.09 (1H, m), 5.12 (1H, br s), 5.29–5.50 (1H, m), 5.54–5.72 (1H, m), 7.18–7.38 (5H, m).

DESCRIPTION 6

(2RS,3SR) Methyl 1-tert-butyloxycarbonyl-2-phenyl-3-(3-phenylthiopropyl)piperidine-3-carboxylate A mixture of the product of Description 5 (0.57 g, 1.6 mmol), thiophenol (2 ml), and AIBN (0.13 g, 0.8 mmol) was stirred at 80° C. under nitrogen for 1.5 hours. On cooling, the mixture was diluted with diethyl ether (25 ml) and washed with aqueous sodium hydroxide solution (4M, 3×10 ml), dried over MgSO$_4$, evaporated, and chromatographed on silica gel, eluting with 9:1 hexanes-ethyl acetate to provide the product as a colourless semi-solid (0.68 g, 92%). $^1$H NMR (360 MHz, CDCl$_3$) δ 1.38–1.67 (4H, m), 1.49 (9H, s), 1.91 (1H, br d, J 15.6 Hz), 1.97 (1H, dd, J 12.2, 4.4 Hz), 2.12 (1H, dt, J 13.5, 4.4 Hz), 2.25 (1H, dt, J 13.5, 5.2 Hz), 2.67 (1H, dt, J 13.5, 3.9 Hz), 2.80–3.01 (2H, m), 3.40 (3H, s), 3.83–4.08 (1H, m), 5.28–5.48 (1H, m), 7.15–7.33 (10H, m); MS (ES$^+$) m/z 370 (M+H-100)).

DESCRIPTION 7

(2RS,3SR) Methyl 1-tert-butyloxycarbonyl-2-phenyl-3-(3-phenylsulfoxypropyl)piperidine-3-carboxylate To an ice-cold solution of the sulfide from the preceding Description 6 (0.67 g, 1.4 mmol) in methanol (25 ml), was added sodium periodate (0.32 g, 1.5 mmol) in water (7.5 ml). The mixture was then stirred at ambient temperature for 24 hours before being filtered, the filtrate evaporated to remove methanol, and the aqueous residue diluted with water (10 ml) and extracted with dichloromethane (3×15 ml). The combined extracts were dried over MgSO$_4$ and evaporated to give a colourless foam (0.63 g, 92%). $^1$H NMR (360 MHz, CDCl$_3$) δ 1.38–1.73 (4H, m), 1.47 (9H, s), 1.87–2.05 (2H, m), 2.11–2.36 (2H, m), 2.62–2.82 (3H, m), 3.38 and 3.44 (3H, 2×s), 3.87–4.02 (1H, m), 5.25–5.64 (1H, m), 7.21–7.28 (5H, m) 7.51–7.54 (3H, m), 7.60–7.63 (2H, m); MS (ES$^+$) m/z 486 (M+H).

DESCRIPTION 8

(5RS,6SR)-7-tert-Butyloxycarbonyl-6-phenyl-7-azaspiro[4.5]dec-3-enone

To a solution of the sulfoxide of Description 7 (1.92 g, 4.0 mmol) in THF (30 ml) cooled to −78° C. was added a solution of lithium hexamethyldisilazide in THF (1M, 10 ml), and the mixture stirred for 1 hour at −78° C. and 1.5 hours at room temperature. Thin layer chromatography at this point indicated remaining starting material, and so more lithium hexamethyldisilazide solution (5 ml) was added and stirring continued for a further 1 hour before evaporating the reaction mixture under reduced pressure. The residue was partitioned between aqueous ammonium chloride (half saturated; 50 ml) and dichloromethane (3×12 ml). The combined organic layers were washed with brine (25 ml), dried over MgSO$_4$ and evaporated to leave a brown gum. This was dissolved in pyridine (25 ml), the resulting solution stirred at reflux for 2 hours, and evaporated. The residue was partitioned between aqueous sodium carbonate (half saturated; 50 ml) and ethyl acetate (20 ml), the aqueous layer extracted with ethyl acetate (10 ml), and the combined organic layers washed with aqueous citric acid (10%, 10 ml) and brine (10 ml). After drying over MgSO$_4$ and evaporating, the residue was chromatographed on silica gel, eluting with 7:3 hexanes-ethyl acetate to leave the desired enone as a colourless solid (1.05 g, 85%). $^1$H NMR (360 MHz, CDCl$_3$) δ 1.37 (9H, s), 1.38–1.44 (1H, m), 1.75 (1H, ddd, J 13.6, 9.5, 5.4 Hz), 1.91 (1H, br d, J 13.6 Hz), 2.40 (1H, dt, J 13.8, 4.4 Hz), 2.58 (1H, dt, J 18.7, 2.3 Hz), 2.90 (1H, ddd, J 18.7, 2.9, 1.9 Hz), 3.28 (1H, dt, J 13.5, 2.9 Hz), 4.10 (1H, dd, J 13.6, 5.1 Hz), 4.85 (1H, br s), 6.12 (1H, dt, J 5.8, 2.0 Hz), 7.22–7.35 (5H, m), 7.67 (1H, dt, J 5.8. 2.7 Hz).

DESCRIPTION 9

2-Bromo-4-(trifluoromethoxy)cyclopropoxybenzene (a) 1-(2-Bromoethoxy)-4-(trifluoromethoxy)benzene 4-(Trifluoromethoxy)phenol (15 g), 2-bromoethanol (7.76 g) and triphenylphosphine (22.1 g) were dissolved in tetrahydrofuran (250 ml). Diethyl azodicarboxylate (13.3 ml) was added dropwise to the stirred mixture and stirring was continued for 12 hours. The mixture was concentrated in vacuo to give a yellow oil. The oil was diluted with hexane to precipitate the triphenylphosphine oxide by-product which was removed by filtration. The filtrate was concentrated and purified on silica using 10% ether in hexane as eluant to give the product (18.35 g). $^1$H NMR (250 MHz, CDCl$_3$) δ 3.63 (2H, t, J 6.1 Hz), 4.30 (2H, t, J 6.2 Hz), 6.84–6.95 (2H, m), 7.12–7.17 (2H, m).

(b) 4-(Trifluoromethoxy)ethenyloxybenzene

The bromide described in step (a) (18.35 g) was dissolved in dichloromethane (90 ml) and the solution was cooled to 0° C. Sodium hydroxide (92 ml, 50% aqueous solution) and tetrabutylammonium hydrogensulfate (21.85 g) were added and the resulting solution was stirred at 0° C. for 3 hours. The reaction mixture was diluted with water (200 ml) and organic layer was separated. The aqueous layer was extracted with dichloromethane and the organic extracts were combined and washed with brine, dried (MgSO$_4$) and concentrated. The residue was purified on silica using hexane as eluant to give the product as a clear oil (9.1 g). $^1$H NMR (360 MHz, CDCl$_3$) δ 4.48 (1H, dd, J 6.0, 1.8 Hz), 4.79 (1H, dd, J 13.6, 1.8), 6.84–6.95 (2H, dd, J 13.6, 6.0).

(c) 4-(Trifluoromethoxy)cyclopropoxybenzene

The enol ether described in step (b) above (9.07 g) and diiodomethane (35.8 ml) were dissolved in dimethoxyethane (200 ml) under a nitrogen atmosphere. Diethylzinc (23 ml, neat) was added dropwise resulting in a mild exothermic reaction. The reaction mixture was heated at reflux overnight. The mixture was cooled and carefully quenched with ammonium chloride (saturated). The mixture was diluted with water (50 ml) and extracted with ether (3×50 ml). The organic extracts were combined and washed with brine, dried (MgSO$_4$) and concentrated to give the title compound as a clear oil (180 mg). The residue was purified by distillation (T 52–56° C, 5.3 mbar) to give the product as a clear oil (5.3 g).

(d) 2-Bromo-4-(trifluoromethoxy)cyclopropoxybenzene 4-(Trifluoromethoxy)cyclopropoxybenzene (3 g) was dissolved in tetrahydrofuran (100 ml) and the solution was cooled to −78° C. under a nitrogen atmosphere. tert-Butyllithium (22.9 ml, 1.5M in pentane) was added dropwise and the solution was stirred for 3 hours. Dibromotetrafluoroethane (8.2 ml) was added dropwise and the reaction mixture was stirred at −78° C. for 2 hours. The reaction was quenched by the dropwise addition of water (50 ml). The product was extracted with diethyl ether. The combined organic fractions were dried (brine, MgSO$_4$) and concentrated in vacuo. The residue was purified on silica using hexane as eluant, to yield the product as a colourless oil (2.2 g). $^1$H NMR (360 MHz, CDCl$_3$) δ 0.86 (4H, m), 3.79 (1H, m), 7.15 (1H, dd, J 8.9, 2.7 Hz), 7.24 (1H, d, J 8.9 Hz), 7.42 (1H, d, J 2.7 Hz).

DESCRIPTION 10

2-Benzyloxy-5-(trifluoromethoxy)bromobenzene a) 2-Bromo-4-(trifluoromethoxy)phenol To a cooled (0° C.) solution of 4-(trifluoromethoxy)phenol (35.6 g, 0.2 mol) in chloroform (280 ml) was added dropwise a solution of bromine (32 g, 0.2 mol) in chloroform (50 ml). The solution was stirred at 0° C. for 1 hour and at room temperature for 2 hours. Dichloromethane (200 ml) and water (400 ml) were added and the organic phase was washed further with water (400 ml), brine (200 ml) and dried (MgSO$_4$). The solvent was removed and the residue was purified by distillation at reduced pressure to give the title compound. $^1$H NMR (250 MHz, CDCl$_3$) δ 7.38 (1H, d, J 2.1 Hz), 7.13 (1H, dd, J 9.1, 2.1 Hz), 7.03 (1H, d, J 9.1 Hz), 5.53 (1H, s).

b) 2-Benzyloxy-5-(trifluoromethoxy)bromobenzene

2-Bromo-4-(trifluoromethoxy)phenol (5 g, 20 mmol) was dissolved in N,N-dimethylformamide (60 ml), and potassium carbonate (5.4 g, 40 mmol) was added, followed by benzyl bromide (3.5 ml, 30 mmol), and the reaction was stirred at ambient temperature for 15 hours. The reaction was diluted with water (150 ml) and extracted into ethyl acetate (3×60 ml). The combined organic fractions were washed with water (100 ml), brine (100 ml), dried (MgSO$_4$) and evaporated in vacuo. Purification on silica, eluting with 2% and 5% ethyl acetate in hexane gave the title compound as a clear oil (6.7 g, 96%). $^1$H NMR (250 MHz, CDCl$_3$) δ 5.47 (2H, s), 7.23 (1H, d, J 9 Hz), 7.43 (1H, dd J 8.2, 2.9 Hz), and 7.75 (6H, m).

DESCRIPTION 11

(3RS,5RS,6SR) and (3SR,5RS,6SR)-3-(2-Benzyloxy-5-trifluoromethoxy)phenyl-7-tert-butyloxycarbonyl-6-phenyl-7-azaspiro[4.5]decan-1-one Magnesium turnings (2.3 g) were covered with tetrahydrofuran (5 ml) and activated with dibromoethane (2×0.1 ml) under a nitrogen atmosphere. The compound of Description 10b (11.1 g, in 15 ml THF) was added dropwise to the stirred magnesium until an exothermic reaction took place and was then added at such a rate as to maintain a gentle reflux. When addition was complete the mixture was heated at reflux for 1 hour and then cooled. Copper(I)iodide (3.1 g) was slurried in tetrahydrofuran and the stirred mixture was cooled to −78° C. under a nitrogen atmosphere. The preformed Grignard reagent was added to the slurry and the mixture was warmed to 0° C. and then recooled to −78° C. The enone of Description 8 (3.6 g in 10 ml THF) was added to the reaction mixture dropwise; thin layer chromatography revealed that all starting material had reacted. The reaction was quenched with ammonium chloride (saturated aqueous solution, 100 ml) and stirred until the aqueous layer turned blue. The mixture was filtered through Celite™ to remove insoluble inorganic material and the excess tetrahydrofuran was removed in vacuo. The aqueous residue was extracted with ethyl acetate (3×100 ml) and the combined organic extracts were dried (brine, MgSO$_4$) and concentrated in vacuo. The resulting oil was purified by chromatography on silica using 10–20% ethyl acetate in hexane to give the product as an inseparable mixture of epimers at C3 (15:1, 4.2 g). Data for the more abundant epimer are as follows: $^1$H NMR (400 MHz, CDCl$_3$) δ 1.31 (9H, s), 1.54–1.60 (1H, m), 2.22–2.32 (2H, m), 2.46 (1H, dd J 17.9, 12.1 Hz), 2.52–2.63 (2H, m), 3.28–3.38 (1H, m), 3.59–3.71 (1H, m), 4.02–4.12 (1H, m), 5.02 (1H, s), 5.10 (2H, s), 6.92 (1H, d, J 9.2 Hz), 7.08 (2H, m), 7.24–7.30 (3H, m) 7.34–7.40 (7H, m). MS (ES$^+$) m/z 596 (M+H, 5%), 540 (M+H-56, 100%), 496 (M+H-100, 50%).

DESCRIPTION 12

(3RS,5RS,6SR)-3-(2-Hydroxy-5-trifluoromethoxy)phenyl-7-tert-butyloxycarbonyl-6-phenyl-7-azaspiro[4.5]decan-1-one The compound of Description 11 (1.9 g, mixture of epimers at C3) was dissolved in methanol (50 ml) in a Parr flask and palladium hydroxide (200 mg) was added. The mixture was hydrogenated at 40 psi for 4 hours. Thin layer chromatography suggested some starting material was still present, thus the mixture was filtered to remove the catalyst and fresh catalyst was added (200 mg) and the mixture was hydrogenated for a further 2 hours. The mixture was filtered and concentrated. The residue was purified by medium pressure chromatography on silica using 6% ethyl acetate in dichloromethane as eluant. This afforded the title compound as the second compound to elute. $^1$H NMR (400 MHz, CDCl$_3$) δ 1.34 (9H, s), 1.55–1.63 (1H, m), 1.76–1.88 (2H, m), 2.31–2.42 (2H, m), 2.48–2,63 (3H, m), 3.27–3.37 (1H, m), 3.45–3.55 (1H, m), 4.02–4.13 (1H, m), 5.18 (1H, s), 5.45 (1H, s, OH), 6.74 (1H, d, J 8.4 Hz), 7.00 (1H, d br), 7.04 (1H, s br), 7.23–7.32 (3H, m) 7.38–7.43 (2H, m). MS (ES$^+$) m/z 523 (M+H, 10%), 450 (M+H-56, 80%), 406 (M+H-100, 100%).

DESCRIPTION 13

(3SR,5RS,6SR)-3-(2-Hydroxy-5-trifluoromethoxy)phenyl-7-tert-butyloxycarbonyl-6-phenyl-7-azaspiro[4.5]decan-1-one The crude product from the reaction of Description 12 was purified by medium pressure chromatography on silica using 6% ethyl acetate in dichloromethane as eluant. This afforded the title compound, the minor epimer, as the first compound to elute. $^1$H NMR (400 MHz, CDCl$_3$) δ 1.45–1.52 (2H, m), 1.48 (9H, s), 1.62–1.72 (1H, m), 1.73–1.80 (1H, m), 2.48 (1H, dd), 2.58 (1H, dd), 2.74 (1H, dd), 2.83 (1H, dd), 3.03 (1H, ddd), 3.95–4.09 (2H, m), 5.15 (1H, s), 6.15 (1H, OH), 6.81 (1H, d), 6.96–7.04 (2H, m), 7.26–7.33 (3H, m), 7.45–7.50 (2H, m). MS (ES$^+$) m/z 523 (M+H, 10%), 450 (M+H-56, 80%), 406 (M+H-100, 100%).

DESCRIPTION 14

2-(2,2,2-Trifluoroethoxy)-5-(trifluoromethoxy)bromobenzene

The compound of Description 10a (2 g), potassium carbonate (2.15 g) and 2,2,2-trifluoroethyltrichloromethane sulfonate (0.101 g) were stirred in dimethylformamide (15 mL) at 60° C. for 2 hours. The reaction was diluted with water and extracted into ethyl acetate. The combined organic extracts were washed with water, brine, dried (magnesium sulfate) and concentrated in vacuo. Purification on silica, eluting with hexane afforded the title compound as a clear oil (2.25 g). $^1$H NMR (360 MHz, CDCl$_3$) δ 4.39 (2H, q, J 8.0 Hz), 6.94 (1H, d, J 9.0 Hz), 7.18 (1H, dd, J 9.0, 3.0 Hz), 7.48 (1H, d, J, 3.0 Hz).

DESCRIPTION 15

2-Benzyloxy-5-(5-(trifluoromethyl)tetrazolyl)iodobenzene (a) 2-Benzyloxy-5-nitroiodobenzene Chloramine-T trihydrate (36 g, 127 mmol) was added to a mixture of 4-nitrophenol (15 g, 107 mmol) and sodium iodide (19.1 g, 127 mmol) in DMF (300 ml) at room temperature. The resulting dark red mixture was stirred at room temperature for 3 hours, poured into water (1.2 L), acidified to pH 1 with aqueous hydrochloric acid (1M) and extracted with ethyl acetate. The organic extract was washed with sodium thiosulphate solution (10%) and brine, dried (MgSO$_4$) and the solvent was evaporated under reduced pressure. The residue was purified by flash column chromatography on silica gel eluting with hexane/ethyl acetate (50:50). The residue was dissolved in DMF (75 ml) and benzyl bromide (10.7 ml, 90 mmol) and potassium carbonate (66 g, 480 mmol) were added. The mixture was stirred at room temperature over night, poured into water (1 L) and extracted with ethyl acetate. The organic extract was washed with brine, dried (MgSO$_4$), and the solvent was evaporated under reduced pressure. The residue was purified by flash column chromatography on silica gel eluting with 1% ethyl acetate in hexane-dichloromethane (50:50) to give the title compound as a colorless solid (24.3 g, 64%). $^1$H NMR (360 MHz, CDCl$_3$) δ 8.70 (1H, d, J 2.7 Hz), 8.21 (1H, dd, J 9.13, 2.7 Hz), 7.48–7.34 (5H, m), 6.89 (1H, d, J 9.14 Hz), 5.27 (2H, s).

(b) 4-Benzyloxy-3-iodoaniline

Iron powder (12.5 g, 224 mmol) was added to a suspension of 2-benzyloxy-5-nitroiodobenzene (10 g, 28 mmol) in water (300 ml) and acetic acid (75 ml) and the mixture was stirred at −80° C. for 12 hours. The mixture was allowed to cool to room temperature and filtered through Hyflo™, washing with 4:1 water:acetic acid and ethyl acetate. The filtrate was extracted with ethyl acetate, and the organic extract was evaporated under reduced pressure. Saturated aqueous sodium hydrogen carbonate was added and the mixture was extracted with ethyl acetate. The organic extract was washed with brine, dried (MgSO$_4$), and the solvent was evaporated under reduced pressure to give the title compound as a brown oil (9 g, 99% yield). $^1$H NMR (360 MHz, CDCl$_3$) δ 7.49–7.47 (2H, m), 7.40–7.28 (3H, m), 7.19 (1H, d, J 2.4 Hz), 6.70 (1H, d, J 8.6 Hz), 6.62 (1H, dd, J 2.4, 8.6 Hz), 5.04 (2H, s). MS (ES$^+$) m/z 326 (M+H).

(c) N-(4-Benzyloxy-3-iodophenyl)trifluoroacetamide

The aniline described in step (b) above (5 g) was dissolved in dichloromethane (50 ml) and triethylamine was added. The mixture was cooled to 0° C. and trifluoroacetic anhydride (2.6 ml) was added dropwise. The mixture was stirred overnight and was then poured onto water and extracted with dichloromethane. The organic extracts were combined and washed with brine, dried (MgSO$_4$) and concentrated to give a brown solid. This was purified on silica using 25% ethyl acetate in hexane to afford a light brown solid which was recrystallised from ethyl acetate in hexane to afford the product as an off-white solid (5.3 g). $^1$H NMR (360 MHz, CDCl$_3$) δ 7.96 (1H, d, J 2.6 Hz), 7.73 (1H, br s), 7.54 (1H, dd, J 8.8, 2.6 Hz), 7.48–7.31 (5H, m), 6.85 (1H, d, J 8.8 Hz), 5.16 (2H, s).

(d) 2-Benzyloxy-5-(5-(trifluoromethyl)tetrazolyl)iodobenzene

The trifluoroacetamide described in step (c) above (8 g) was suspended in carbon tetrachloride (150 ml) and was heated at reflux under nitrogen. Triphenylphosphine (9.96 g) was added and the reaction mixture was heated for a further 12 hours. The mixture was cooled and concentrated in vacuo. The residue was heated at reflux in hexane (150 ml) for 1 hour, cooled and filtered to remove triphenylphosphine oxide. The filtrate was concentrated in vacuo to give a yellow oil (6.5 g) which was not purified further. This chloroimidate intermediate was dissolved in dimethylformamide (20 ml) and the solution was added dropwise to a suspension of sodium azide (1.2 g) in dimethylformamide. This mixture was stirred for 18 hours and then was poured onto water. The mixture was extracted with ethyl acetate (3×20 ml). The organic extracts were combined and washed with brine, dried (MgSO$_4$) and concentrated to give a yellow oil. This was purified on silica using 35% ethyl acetate in hexane to afford the title compound as a yellow oil (6.1 g). $^1$H NMR (360 MHz, CDCl$_3$) δ 5.26 (2H, s), 7.00 (1H, d, J 8.8 Hz), 7.51–7.35 (6H, m), 7.93 (1H, d, J 2.6 Hz).

DESCRIPTION 16

(3RS,5RS,6SR) and (3SR,5RS,6SR)-3-(2-Benzyloxy-5-(5-trifluoromethyl)tetrazolyl)phenyl-6-phenyl-7-tert-butyloxycarbonyl-7-azaspiro[4,5]decan-1-one The compound of Description 15 (4.09 g), the compound of Description 8 (1.0 g), lithium chloride (0.771 g), tetra-n-butylammonium chloride (1.02 g) and potassium formate (0.77 g) were dissolved in dimethylformamide (10 mL) and water (0.1 mL) and degassed. Palladium (II) acetate (0.068 g) was added, the reaction degassed again and then stirred under nitrogen at 45° C. for 48 hours. The reaction mixture was cooled then filtered through Celite™. The filtrate was diluted with ethyl acetate, water added and the product extracted into ethyl acetate. The combined organic extracts were washed with water, brine, dried (magnesium sulfate), and concentrated in vacuo to afford the product as a dark brown oil. The oil was purified on silica, eluting with 10% ethyl acetate in hexane to afford the title compound as an off white foam (1.26 g, mixture of epimers at C3). MS (ES$^+$) m/z 648 (M+1H).

DESCRIPTION 17

(3RS,5RS,6SR)-3-(2-Hydroxy-5-(5-trifluoromethyl)tetrazolyl)-phenyl-7-tert-butyloxycarbonyl-6-phenyl-7-azaspiro[4,5]decan-1-one The compound of Description 16 (1.26 g, mixture of epimers at C3) was dissolved in the minimum of ethyl acetate in a Parr flask and methanol (35 mL) added. The reaction vessel was degassed then palladium (II) hydroxide on activated charcoal added and the mixture was hydrogenated at 40 psi for 3.5 hours. Thin layer chromatography suggested some starting material still present, thus the mixture was filtered to remove the catalyst, fresh catalyst added and the mixture hydrogenated for a further 3.5 hours. The reaction mixture was filtered through Celite™ and the filtrate concentrated in vacuo to afford the product as a yellow foam, containing a mixture of epimers. The epimers were separated by medium pressure chromatography, eluting with 40% ethyl acetate in hexane, to afford the title compound as the second compound to elute (650 mg). $^1$H NMR (400 MHz, CDCl$_3$) δ 1.60–1.67 (1H, m), 1.78–1.86 (2H, m), 2.28–2.37 (1H, m), 2.40–2.48 (1H, m), 2.55–2.68 (3H, m), 3.34–3.43 (1H, m), 3.50–3.59 (1H, m), 4.04–4.13 (1H, m), 5.20 (1H, s), 6.86 (1H, d, J 8.5 Hz), 7.16 (1H, dd, J 8.5, 2.6 Hz), 7.24–7.28 (4H, m), 7.38–7.40 (2H, m). MS (ES$^+$) m/z 558 (M+H).

DESCRIPTION 18

(3SR,5RS,6SR)-3-(2-Hydoxy-5-(5-trifluoromethyl)tetrazoyl)phenyl-7-tert-butyloxycarbonyl-6-phenyl-7-azaspiro[4,5]decan-1-one The crude product from the reaction of Description 17 was purified by medium pressure chromatography on silica, eluting with 40% ethyl acetate in hexane. This afforded the title compound, the minor epimer, as the first compound to elute (82 mg). $^1$H NMR (400 MHz, CDCl$_3$) δ 1.46–1.52 (1H, m), 1.64–1.73 (1H, m), 1.77–1.83 (1H, m), 2.38–2.46 (2H, m), 2.53–2.62 (1H, m), 2.73–2.80 (1H, m), 2.89–2.97 (1H, m), 3.04–3.13 (1H, m), 4.00–4.07 (1H, m), 5.68 (1H, s), 6.98 (1H, d, J 8.6 Hz), 7.20 (1H, dd, J 8.6, 2.5 Hz), 7.26–7.30 (4H, m), 7.44–7.46 (2H, m), MS (ES$^+$) m/z 558 (M+H).

DESCRIPTION 19

(3RS,5RS,6SR)-3-(2-Difluoromethoxy-5-(5-trifluoromethyl)-tetrazolyl)phenyl-7-t-butyloxycarbonyl-6-phenyl-7-azaspiro[4,5]decan-1-one The compound from Description 17 (0.354 g) and potassium carbonate (0.26 g) were stirred in dimethylformamide (2.5 mL) at 110° C. Isopropylchlorodifluoroacetate (0.22 g) was added dropwise and the reaction stirred at 110° C. for 1 hour. The reaction was quenched with water and the product extracted into ethyl acetate. The combined organic extracts were washed with water, brine, dried (magnesium sulfate) and concentrated in vacuo to afford the product as a yellow oil. The oil was purified on silica, eluting with 10% ethyl acetate in hexane to afford the title compound as a white foam (0.18 g). MS (ES$^+$) m/z 608 (M+H).

DESCRIPTION 20

(3SR,5RS,6SR)-3-(2-Difluoromethoxy-5-(5-trifluoromethyl)-tetrazolyl)phenyl-7-tert-butyloxycarbonyl-6-phenyl-7-azaspiro[4,5]decan-1-one The compound of Description 18 was reacted according to the conditions of Description 19. The crude product was purified on silica, eluting with 15% ethyl acetate in hexane to afford the title compound as a pale yellow oil. MS (ES$^+$) m/z 608 (M+H).

EXAMPLE 1

(3RS,5RS,6SR)-3-(2-Methoxy-5-trifluoromethoxy)phenyl-6-phenyl-7H-azaspiro[4.5]decan-1-one Hydrochloride a) (3RS,5RS,6SR)-7-tert-Butyloxycarbonyl-3-(2-methoxy-5-trifluoromethoxy)phenyl-6-phenyl-7-azaspiro[4.5]decan-1-one 2-Bromo-4-trifluoromethoxyanisole (813 mg, 3 mmol) was added dropwise with stirring over 30 minutes to magnesium turnings (75 mg, 3.1 mmol) in dry THF (4 ml) containing a trace of iodine. After 1.5 hours, the resulting yellow solution was added to a suspension of copper(I) iodide (295 mg, 1.55 mmol) in THF (3 ml) at −78° C., stirred for 10 minutes, allowed to warm to 0° C., and after a further 10 minutes, recooled to −78° C. A solution of the enone of Description 8 (270 mg, 0.83 mmol) in THF (2 ml) was added, the mixture allowed to warm to room temperature, and stirred for 1.5 hours. Aqueous ammonium chloride (saturated; 10 ml) was added, the mixture stirred for 2 hours, the phases separated, and the aqueous extracted with ethyl acetate (2×10 ml). The combined organic layers were washed with aqueous citric acid (10%, 15 ml), dried over MgSO$_4$, evaporated, and the residue subjected to chromatography on silica gel, eluting with 3:1 isohexane-ethyl acetate to afford the desired product as a pale yellow solid (236 mg, 56%). $^1$H NMR (360 MHz, CDCl$_3$) δ 1.32 (9H, s), 1.57–1.65 (1H, m), 2.17–2.56 (4H, m), 2.55 (1H, dt, J 16.3, 6.9 Hz), 3.32–3.40 (1H, m), 3.51–3.59 (1H, m), 3.84 (3H, s), 4.03–4.15 (1H, m), 5.05 (1H, br s), 6.85 (1H, d, J 8.8 Hz), 7.06–7.12 (2H, m), 7.23–7.32 (3H, m), 7.38 (2H, dd, J 8.2, 1.7).

b) (3RS,5RS,6SR)-3-(2-Methoxy-5-trifluoromethoxy)phenyl-6-phenyl-7H-azaspiro[4.5]decan-1-one Hydrochloride A solution of the compound of step (a) above (70 mg, 0.14 mmol) in dichloromethane (3 ml) containing trifluoroacetic acid (0.15 ml) was stirred for 5 hours, the solution was evaporated, and the residue partitioned between ethyl acetate (10 ml) and aqueous sodium carbonate (saturated; 5 ml). The organic layer was dried over MgSO$_4$, evaporated, and the residue purified by chromatography on silica gel, eluting with 9:1 dichloromethane-methanol, to give the free base as a yellow gum (57 mg). Conversion to the hydrochloride salt gave a colourless solid (MeOH/Et$_2$O; 41 mg). $^1$H NMR (360 MHz, DMSO-d$_6$) δ 1.74–2.8 (5H, m), 2.17 (1H, dd, J 19.0, 11.4 Hz), 2.32 (1H, br d, J 12.2 Hz), 2.66 (1H, dd, J 19.0, 7.9 Hz), 3.01–3.15 (1H, m), 3.35–3.44 (1H, m), 3.44 (3H, s), 3.60–3.74 (1H, m), 4.42 (1H, br s), 6.92 (1H, br s), 6.96 (1h, d, J 9.1 Hz), 7.14–7.21 (1H, m), 7.30–7.38 (2H, m), 7.43–7.53 (3H, m), 8.54 (1H, br s), 9.76 (1H br s); MS (ES$^+$) m/z 420 (M+H).

EXAMPLE 2

(3RS,5RS,6SR)-3-(2-Methoxy-5-trifluoromethoxy)phenyl-6-phenyl-7-(1,2,4-triazol-3-yl)methyl-7-azaspiro[4.5]decan-1-one Hydrochloride The compound of Example 1 (166 mg) was dissolved in dimethylformamide (2 ml) and N-formyl 2-chloroacetamidhydrazone (54 mg) and potassium carbonate (55 mg) were added. The reaction was heated at 60° C. for 14 hours. The reaction mixture was then diluted with xylene (1.5 ml) and heated to 120° C. for 2 hours. The reaction mixture was diluted with water (10 ml) and the product was extracted with dichloromethane. The organic solution was dried (brine, MgSO$_4$) and concentrated in vacuo. The residue was purified on silica using 10% methanol in dichloromethane as eluant. The product obtained was recrystallised from diethyl ether/ethyl acetate to yield the product as a white crystalline solid. $^1$H NMR (360 MHz, CDCl$_3$), δ 1.53 (3H, m), 1.82 (1H, m), 1.94 (1H, dd, J 17.9, 12.7 Hz), 2.14 (1H, t, J 12.5 Hz), 2.24 (2H, m), 2.41 (1H, t, J 11.7 Hz), 2.60 (1H, dd, J 18.1, 7.1 Hz), 3.05 (1H, d), 3.36 (1H, d, J 16.3 Hz), 3.44 (1H, s), 3.52 (1H, q, J 6.7 Hz), 3.62 (3H, s), 3.73 (1H, d, J 16.3 Hz), 6.57 (1H, d), 6.72 (1H, d, J 8.9 Hz), 6.98 (1H, dd, J 8.9 Hz), 7.24 (5H, s), 7.88 (1H, s). MS (ES$^+$) m/z 501 (M+H, 100%).

EXAMPLE 3

(3RS,5RS,6SR)-3-(2-Cyclopropoxy-5-trifluoromethoxy)phenyl-6-phenyl-7-azaspiro[4.5]decan-1-one Hydrochloride (a) (3RS,5RS,6SR)-7-(tert-Butyloxycarbonyl)-3-(2-cyclopropoxy-5-trifluoromethoxy)phenyl-6-phenyl-7-azaspiro[4.5]decan-1-one 2-Bromo-4-(trifluoromethoxy)cyclopropoxybenzene (Description 9) (2.17 g) in tetrahydrofuran (4 ml) was added dropwise to magnesium turnings (196 mg) in tetrahydrofuran at such a rate as to maintain reflux. The reaction was stirred for 2 hours with occasional heating. The Grignard reagent thus formed was allowed to cool to room temperature and was added to a slurry of copper(I)iodide (698 mg) in tetrahydrofuran (8 ml) pre-cooled to −78° C. The reaction was stirred at −78° C. for 1 hour and then allowed to warm to 0° C. The reaction mixture was stirred at 0° C. for 5 mins and then recooled to −78° C. The compound of Description 8 (800 mg), was added as a solution in tetrahydrofuran (3 ml). The reaction mixture was stirred at −78° C. for 2 hours and then was diluted with saturated aqueous ammonium chloride solution (30 ml) and stirred until a blue coloration persisted. The product was extracted with ethyl acetate (3×20 ml). The combined organic fractions were dried (brine, MgSO$_4$) and concentrated in vacuo. The residue was purified on silica using 12% ethyl acetate in hexane to yield two products: epimer A (55 mg) and epimer B (960 mg) as colourless oils. The data for epimer A are as follows: $^1$H NMR (CDCl$_3$, 360 MHz) δ 0.78 (4H, m), 1.42 (9H, s), 1.59 (2H, m), 1.76 (2H, m), 2.26 (1H, dd, J 19.2, 9.6 Hz), 2.51 (1H, td, J 12.1, 5.2 Hz), 2.64 (1H, dd, J 12.9, 5.6 Hz), 2.86 (1H, dd, J 17.8, 8.0 Hz), 3.08 (1H, td, J 12.1, 5.6 Hz), 3.73 (1H, m), 3.82 (1H, m), 4.11 (1H, dt, J 14.1 Hz), 5.44 (1H, s), 7.10 (3H, m), 7.24 (3H, m), 7.41 (2H, d, J 6.8 Hz). MS (ES$^+$) n/z 546 (5%, M+H), 490 (100%, M+H-56), 446 (30%, M+H-100).

The data for epimer B are as follows: $^1$H NMR (CDCl$_3$, 360 MHz) δ 0.70–0.83 (4H, m), 1.32 (9H, s), 1.58 (1H, m), 1.80 (2H, m), 2.28 (2H, m), 2.31 (1H, d, J 8.5 Hz), 2.42 (1H, d, J 9.2 Hz), 2.53 (1H, td, J 16.9, 6.0 Hz), 3.31 (1H, m), 3.46 (1H, m), 3.73 (1H, m), 4.11 (1H, d, J 7.1 Hz), 5.02 (1H, s), 7.05 (1H, d, J 2.7 Hz), 7.10 (1H, dd, J 8.9 Hz), 7.26 (4H, m), 7.36 (2H, d, J 8.3 Hz). MS (ES$^+$) m/z 546 (3%, M+H), 490 (100%, M+H-56), 446 (12%, M+H).

(b) (3RS,5RS,6SR)-3-(2-Cyclopropoxy-5-(trifluoromethoxy))phenyl-6-phenyl-7-azaspiro[4.5]decan-1-one Hydrochloride The compound described in Example 3c, epimer B (960 mg), was dissolved in dichloromethane (2 ml) and hydrogen chloride in methanol added (4N, 5 ml). The reaction was stirred at room temperature for 3 hours. The reaction was diluted with saturated aqueous sodium bicarbonate solution and the product extracted with ethyl acetate (3×20 ml). The combined organic extracts were dried (brine, MgSO$_4$) to give the compound as a yellow solid. $^1$H NMR (CDCl$_3$, 360 MHz) δ 0.59 (2H, m), 0.72 (2H, m), 1.45 (2H, td), 1.85 (2H, m), 2.04 (1H, m), 2.08 (1H, t, J 12.4 Hz), 2.27 (1H, d, J 14.3 Hz), 2.56 (1H, dd, 12.8, 4.9 Hz), 2.80 (1H, td, J 9.9 Hz), 3.34 (1H, dd), 3.49 (1H, sep, J 2.9 Hz), 3.60 (1H, m), 3.64 (1H, s), 6.59 (1H, d), 7.99 (1H, dd, J 9.54), 7.12 (1H, J 8.9, 7.24 (5H, m). MS (ES$^+$) m/z 446 (100%, M+H).

A portion of the free base (30 mg) was dissolved in ethyl acetate and hydrogen chloride in methanol (1N, 1 ml) was added. The resulting solution was concentrated in vacuo and the product was recrystallised from ethyl acetate. $^1$H NMR (CDCl$_3$, 360 MHz) δ 0.54 (2H, m), 0.71 (2H, m), 1.85 (3H, m), 1.99 (1H, m), 2.04 (1H, t, J 13.2 Hz), 2.10 (2H, m), 2.26 (1H, d, J 14.1 Hz), 2.67 (1H, dd, J 16.0, 8.1 Hz), 3.28 (1H, m), 3.56 (1H, s), 3.64 (1H, m), 4.32 (1H, s), 6.59 (1H, s), 7.03 (1H, d), 7.14 (1H, d, J 8.9 Hz), 7.29 (2H, s), 7.39 (3H, s). MS (ES$^+$) m/z 446 (100%, M+H).

EXAMPLE 4

(3SR,5RS,6SR)-3-(2-Cyclopropoxy-5-trifluoromethoxy)phenyl-6-phenyl-7-azaspiro[4.5]decan-1-one Hydrochloride The compound described in Example 3c, epimer A (55 mg), was deprotected and purified according to the method illustrated in Example Ib to afford the title compound as the crystalline hydrochloride salt (15 mg). $^1$H NMR (CDCl$_3$, 360 MHz) δ 0.60–0.64 (2H, m), 0.76–0.80 (2H, m), 1.70–1.85 (3H, m), 1.92–2.02 (1H, m), 2.03–2.16 (1H, m), 2.20–2.32 (1H, m), 2.38–2.50 (2H, m), 2.58 (1H, dd, J 17.8, 12.7 Hz), 3.15 (1H, dt br), 3.54–3.62 (2H, m), 4.24 (1H, s), 6.70 (1H, d, J 2.6 Hz), 7.02 (1H, dd, J 8.8, 2.6 Hz), 7.12 (1H, d, J 8.8 Hz), 7.36 (5H, m); MS (ES$^+$) m/z 446 (M$^+$+H, 100%).

EXAMPLE 5

(3RS,5RS,6SR)-3-(2-Cyclopropoxyoxy-5-trifluoromethoxy)phenyl-6-phenyl-7-(1,2,4-triazol-3-yl)methyl-7-azaspiro[4.5]decan-1-one Hydrochloride The compound of Example 3 (200 mg) was dissolved in dimethylformamide (2 ml) and 2-chloroacetamidhydrazone (67 mg) and potassium carbonate (124 mg) were added. The reaction mixture was heated at 60° C. for 1.5 hours and then xylene (1 ml) was added. The reaction was heated at 120° C. for 2 hours. The reaction was diluted with water (20 ml) and the product extracted with ethyl acetate (3×10 ml). The combined organic extracts were dried (brine, MgSO$_4$) and concentrated in vacuo. The residue was purified on silica using 5% methanol in dichloromethane. The product was recrystallised from ethyl acetate to yield a white solid (100 mg). $^1$H NMR (CDCl$_3$, 360 MHz) δ 0.64 (2H, m), 0.75 (2H, m), 1.56 (2H, m), 1.83 (2H, m), 1.99 (1H, t, J 12.4 Hz), 2.23 (2H, m), 2.42 (1H, td, J 11.6 Hz), 2.58 (1H, dd, J 11.9, 6.9 Hz), 3.04 (1H, d), 3.36 (1H, d, J 16.3 Hz), 3.42 (1H, s), 3.53 (1H, m), 3.62 (1H, m), 3.73 (1H, d, J 16.3 Hz), 6.44 (1H, s), 6.98 (1H, d, J 11.2 Hz), 7.13 (1H, d, J 8.8 Hz), 7.24 (5H, m), 7.88 (1H, s): MS (ES$^+$) m/z 527 (100%, M+H).

EXAMPLE 6

(3SR,5RS,6SR)-3-(2-Methoxy-5-trifluoromethoxy)phenyl-6-phenyl-7H-azaspiro[4.5]decan-1-one Hydrochloride (a) (3RS,5RS,6SR)-7-t-Butyloxycarbonyl-3-(2-methoxy-5-trifluoromethoxy)phenyl-6-phenyl-2-phenylselenyl-7H-azaspiro[4.5]decan-1-one Diisopropylamine (541 μl) was dissolved in tetrahydrofuran (1 ml) and the solution cooled to −78° C. n-Butyllithium (3.61 ml, 1.6M) was added dropwise such that the internal temperature did not exceed −60° C. The reaction mixture was stirred at −78° C. for 30 min. The compound of Example Ia (1 g) was added dropwise as a solution in tetrahydrofuran (2 ml). The reaction mixture was stirred at −78° C. for 2 hours. Phenylselenium bromide (1.91 g) was added as a solution in tetrahydrofuran (3 ml) and the reaction mixture was stirred at −78° C. for 1 hour. The reaction was quenched with saturated aqueous ammonium chloride solution (20 ml) and the product extracted with ethyl acetate (3×20 ml). The residue was purified on silica using 10% ethyl acetate in hexane as eluant to yield the product (a mixture of isomers) as a yellow oil (454 mg). MS (ES$^+$) 676 (10%, M+H), 620 (100%, M+H-56), 576 (15%, M+H-100).

(b) (5RS,6SR)-7-tert-Butyloxycarbonyl-3-(2-methoxy-5-trifluoromethoxy)phenyl-6-phenyl-7H-azaspiro[4.5]dec-2-enone The selenide (454 mg) described in step (a) above was dissolved in tetrahydrofuran (2 ml) and cooled to 0° C. Hydrogen peroxide (1.3 ml. 35% by weight) and potassium carbonate (20 mg) was added and the reaction mixture was stirred at 0° C. for 20 minutes. The reaction mixture was allowed to warm to room temperature and the reaction diluted with saturated aqueous sodium bicarbonate solution (10 ml). The product was extracted with ethyl acetate (3×10 ml). The combined organic extracts were dried (brine, MgSO$_4$) and concentrated in vacuo. The residue was purified on silica using 25% ethyl acetate in hexane as eluant to afford the product enone as a foam. $^1$H NMR (CDCl$_3$, 360 MHz) δ 1.34 (9H, s), 1.53 (1H, d, J 14.2 Hz), 1.82 (2H, m), 1.93 (1H, m), 2.49 (1H, td, J 13.8, 4.6 Hz), 2.89 (1H, dd, J 17.3, 1.8 Hz), 3.22 (1H, d, J 18.1 Hz), 3.30 (1H, td, J 13.2, 3.9 Hz), 3.93 (3H, s), 4.13 (1H, dd, J 7.2 Hz), 4.96 (1H, s), 6.68 (1H, s), 6.99 (1H, d, J 9.1 Hz), 7.28 (4H, m), 7.39 (2H, m).

(c) (3SR,5RS,6SR)-3-(2-Methoxy-5-trifluoromethoxy)phenyl-6-phenyl-7H-azaspiro[4.5]decan-1-one Hydrochloride The enone described in step (b) above (70 mg) was dissolved in tetrahydrofuran (0.5 ml) and methanol (1 ml)

and magnesium turnings (7 mg) were added. The reaction mixture was stirred at room temperature for 16 hours. The reaction was diluted with hydrochloric acid (1N, 3 ml) and the product extracted with ethyl acetate (3×5 ml). The combined organic extracts were dried (brine, MgSO$_4$) and concentrated in vacuo. The residue was purified on silica using 20% ethyl acetate in hexane as eluant to yield the product as a colourless oil (22 mg). $^1$H NMR (CDCl$_3$, 360 MHz) δ 1.44 (9H, s), 1.62 (1H, m), 1.73 (3H, m), 2.30 (1H, dd, J 19.2, 9.9 Hz), 2.51 (1H, td, J 13.9, 4.5 Hz), 2.70 (1H, dd, J 12.9, 6.9 Hz), 2.82 (1H, dd, J 19.2, 7.9 Hz), 3.09 (1H, td, J 13.4, 3.5 Hz), 3.84 (3H, s), 3.95 (1H, m), 4.08 (1H, dd, J 14.8 Hz), 5.48 (1H, s), 6.85 (1H, d, J 8.7 Hz), 7.06 (1H, s), 7.09 (1H, d, J 9.1 Hz), 7.28 (3H, m), 7.43 (2H, d, J 6.9 Hz).

The free base (22 mg) was dissolved in hydrogen chloride in methanol (4N, 1 ml) and the reaction mixture was stirred at room temperature for 1 hour. The reaction was concentrated in vacuo and the product was recrystallised from ethyl acetate (10 mg) to afford the title compound as white crystals. $^1$H NMR (CDCl$_3$, 500 MHz) δ 0.63 (3H, m), 0.98 (1H, d, J 15 Hz), 1.05 (1H, m), 2.28 (1H, dd, J 15, 5 Hz), 2.48 (1H, dd, J 15, 5 Hz), 2.66 (1H, dd, J 15, 5 Hz), 3.18 (1H, t, J 10 Hz), 3.60 (1H, d, J 15 Hz), 3.70 (3H, s), 4.24 (1H, s), 6.73 (2H, m), 7.02 (1H, d, J 10 Hz), 7.40 (5H,m); MS (ES$^+$) m/z 420 (100%, M+H).

EXAMPLE 7

(3RS,5RS,6SR)-3-(2-Isopropoxy-5-trifluoromethoxy)phenyl-6-phenyl-7-azaspiro[4,5]decan-1-one The compound of Description 12 (280 mg) was dissolved in dimethylformamide (2 ml) and potassium carbonate (180 mg) and iodopropane (110 μl) were added. The mixture was stirred at 80° C. for 12 hours. The mixture was diluted with water (50 ml) and extracted with ethyl acetate (3×20 ml). The organic extracts were combined and washed with brine, dried (MgSO$_4$) and concentrated to give an oil. This was purified by chromatography on silica using 2–3% ethyl acetate in dichloromethane as eluant to afford the product as a clear oil (200 mg). This was deprotected with trifluoroacetic acid according to the procedure described in Example Ib to afford the title compound (148 mg). $^1$H NMR (400 MHz, CDCl$_3$) δ 1.20 (3H, d, J 6.0 Hz), 1.24 (3H, d, J 6.0 Hz) 1.58–1.66 (2H, m), 1.82–1.94 (2H, m), 2.01–2.13 (2H, m), 2.27–2.32 (1H, m), 2.58–2.65 (1H, m) 2.80–2.87 (1H, m, 3.38 (1H, dd, J 12.7, 4.5 Hz), 3.53–3.63 (1H, m), 3.69 (1H, s), 4.45 (1H, hept, J 6.0 Hz), 6.60 (1H, d, J 2.6 Hz), 6.74 (1H, d, J 9.0 Hz), 6.96 (1H, dd, J 9.0, 2.2 Hz), 7.22–7.32 (5H, m); MS (ES$^+$) m/z 448 (M+H).

EXAMPLE 8

(3RS,5RS,6SR)-3-(2-Isopropoxy-5-trifluoromethoxy)phenyl-6-phenyl-7-(1,2,4-triazol-3-yl)methyl-7-azaspiro[4,5]decan-1-one The compound of Example 7 was reacted according to the procedure described in Example 2 to afford the title compound. $^1$H NMR (400 MHz, CDCl$_3$) δ 1.25 (3H, d, J 6.0 Hz), 1.28 (3H, d, J 6.0 Hz), 1.48–1.64 (2H, m), 1.78 (1H, dd, J 17.8,13 Hz), 1.86 (1H, ddd, J 16.8, 6.4, 6.5, 2.1 Hz), 1.97 (1H, dd, J 12.4, 12.4 Hz), 2.20–2.29 (2H, m), 2.40–2.47 (1H, m), 2.63 (1H, ddd, J 17.9, 7.0, 2.0 Hz), 3.07 (1H, d, J 11.3 Hz), 3.36 (1H, d, J 16.3 Hz), 3.44 (1H, s), 3.56–3.64 (1H, m), 3.73 (1H, d, J 16.3 Hz), 4.47 (1H, hept, J 6.0 Hz), 6.48 (1H, d, J 2.8 Hz), 6.74 (1H, d, J 9.0 Hz), 6.95 (1H, dd, J 9.0, 2.2 Hz), 7.26–7.35 (5H, m); MS (ES$^+$) m/z 529 (M+H).

EXAMPLE 9

(3RS,5RS,6SR)-3-(2-Hydroxy-5-trifluoromethoxy)phenyl-6-phenyl-7-azaspiro[4,5,]decan-1-one This compound was prepared by deprotection of the compound of Description 12 according to the procedure of Example Ib. MS (ES$^+$) m/z 406 (M+H, 100%).

EXAMPLE 10

(3RS,5RS,6SR)-3-(2-Cyclopropylmethyloxy-5-trifluoromethoxy)phenyl-6-phenyl-7-azaspiro[4,5,]decan-1-one This compound was prepared by alkylation of the compound of Description 12 following the procedure of Description 19 and subsequent deprotection according to the procedure of Example Ib. $^1$H NMR (400 MHz, CDCl$_3$) δ 0.27–0.30 (2H, m), 0.53–0.61 (2H, m), 1.53–1.75 (4H, m), 1.83–1.92 (2H, m), 2.00–2.12 (1H, m), 2.29–2.33 (1H, br d), 2.64 (1H, ddd, J 17.9, 4.9, 2.2 Hz), 2.81 (1H, ddd, J 13.0, 13.0, 3.04), 3.38 (1H, br dd), 3.58–3.76 (4H, m), 6.55–6.60 (1H, m), 6.72 (1H, d, J 8.9 Hz), 6.92–6.99 (1H, m), 7.18–7.30 (7H, m); MS (ES$^+$) m/z 460 (M+H, 100%).

EXAMPLE 11

(3RS,5RS,6SR)-3-(2-Difluoromethoxy-5-trifluoromethoxy)phenyl-6-phenyl-7-azaspiro[4,5]decan-1-one This compound was prepared by alkylation of the compound of Description 12 with cyclopropylmethyl bromide following the procedure of Description 19 and subsequent deprotection according to the procedure of Example Ib. $^1$H NMR (400 MHz, CDCl$_3$) δ 1.57–1.67 (2H, m), 1.80 (1H, dd, J 18.0, 12.7 Hz), 1.88–1.93 (1H, m), 2.06 (1H, t, J 12.4 Hz), 2.19–2.29 (2H, m), 2.61 (1H, ddd, J 17.9, 7.3, 1.9 Hz), 2.82 (1H, ddd, J 13.0, 13.0, 3.0 Hz), 3.38 (1H, dd, J 13.0, 4.1 Hz), 3.60–3.70 (2H, m), 6.36 (1H, t, J 73.0 Hz), 6.55 (1H, d, J 2.4 Hz), 7.02 (1H, dd, J 8.9, 2.1 Hz), 7.08 (1H, d, J 8.9 Hz), 7.23–7.35 (5H, m); MS (ES$^+$) m/z 456 (M+H).

EXAMPLE 12

(3RS,5RS,6SR)-3-(2-Difluoromethoxy-5-trifluoromethoxy)phenyl-6-phenyl-7-(1,2,4-triazol-3-yl)methyl-7-azaspiro[4,5]decan-1-one The compound of Example 11 was reacted according to the procedure described in Example 2 to afford the title compound. $^1$H NMR (360 MHz, CDCl$_3$) δ 1.48–1.64 (2H, m), 1.72–1.81 (1H, m), 1.88–2.02 (2H, m), 2.20–2.32 (2H, m), 2.42–2.52 (1H, m), 2.60 (1H, dd, J 17.9, 5.5 Hz), 3.05 (1H, m), 3.39 (1H, d, J 16.3 Hz), 3.47 (1H, s), 3.65 (1H, m), 3.76 (1H, d, J 16.3 Hz), 6.39 (1H, t, J 73.0 Hz), 6.44 (1H, d, J 2.2 Hz), 7.01 (1H, dd, J 8.9, 2.2 Hz), 7.07 (1H, d, 8.9 Hz), 7.26–7.31 (5H, m), 7.89 (1H, s); MS (ES$^+$) m/z 537 (M+H)

EXAMPLE 13

(3RS,5RS,6SR)-6-Phenyl-3-(2-(2,2,2-trifluoroethoxy-5-trifluoromethoxy)phenyl-7-azaspiro[4,5,]decan-1-one This compound was prepared by the reaction of the enone of Description 8 and 2-(2,2,2-trifluoroethoxy)-5-(trifluoromethoxy)bromobenzene (Description 14) according to the procedure described in Example 1. $^1$H NMR (400 MHz, CDCl$_3$) δ 1.57–1.66 (2H, m), 1.81 (1H, dd, J 17.8, 12.9 Hz), 1.89–2.14 (3H, m), 2.29 (1H, d, J 13.8 Hz), 2.61 (1H, ddd, J 17.8, 7.1, 1.9 Hz), 2.81 (1H, ddd, J 18.2, 18.2, 3.0 Hz), 3.37 (1H, dd, J 13.0, 4.4 Hz), 3.60–3.70 (2H, m), 4.20–4.35 (2H, m), 6.60 (1H, d, J 2.6 Hz), 6.74 (1H, d, J 8.9 Hz), 7.01 (1H, dd, J 8.9, 2.6 Hz), 7.21–7.32 (5H, m); MS (ES$^+$) m/z 488 (M$^+$1H).

EXAMPLE 14

(3RS,5RS,6SR)-6-Phenyl-7-(1,2,4-triazol-3-yl) methyl-3-(2-(2,2,2-trifluoroethoxy-5-trifluoromethoxy)phenyl-7-azaspiro[4,5]decan-1-one The compound of Example 13 was reacted according to the procedure described in Example 2 to afford the title compound. $^1$H NMR (400 MHz, CDCl$_3$) δ 1.48–1.61 (2H, m), 1.77 (1H, dd, J 17.6, 13.0 Hz), 1.86–1.96 (2H, m), 2.19–2.29 (2H, m), 2.46 (1H, ddd, J 12.4, 12.4, 2.6 Hz), 2.61 (1H, dd, J 17.7, 7.2 Hz), 3.07 (1H, d, J 12.0 Hz), 3.38 (1H, d, J 16.4 Hz), 3.45 (1H, s), 3.62–3.70 (1H, m), 3.74 (1H, d, J 16.4Hz), 4.22–4.36 (2H, m), 6.50 (1H, d, J 2.5 Hz), 6.75 (1H, d, J 9.0 Hz), 7.01 (1H, dd, J 8.8, 2.2 Hz), 7.25–7.30 (5H, m); MS (ES$^+$) m/z 569 (M+H).

EXAMPLE 15

(3SR,5RS,6SR)-3-(3,5-Dimethyl)phenyl-6-phenyl-7-azaspiro[4,5]decan-1-one

This compound was prepared by the reaction of the enone of Description 8 and 3-bromo-m-xylene according to the procedure described in Example 1. $^1$H NMR (400 MHz, CDCl$_3$) δ 1.75–2.15 (6H, m), 2.16–2.32 (7H,m), 2.79 (1H, ddd, J 19.2, 7.5, 1.8), 3.28–3.44 (2H, m), 3.50 (1H, dd, J 12.7, 4.3), 4.37 (1H, s), 6.48 (1H, s), 6.82 (1H, s), 7.20–7.23 (2H, m), 7.34–7.38 (3H, m); MS (ES$^+$) m/z 334 (M+H, 100%).

EXAMPLE 16

(3SR,5RS,6SR)-3-(3,5-Dimethyl)phenyl-6-phenyl-7-(1,2,4-triazol-3-yl)methyl-7-azaspiro[4,5]decan-1-one The compound of Example 15 was reacted according to the procedure described in Example 2 to afford the title compound. $^1$H NMR (400 MHz), CDCl$_3$) δ 1.50–1.59 (2H, m), 1.83–1.92 (2H, m), 1.99–2.05 (1H, m), 2.20–2.25 (8H, m), 2.38–2.44 (1H, m), 2.60 (1H, br dd), 3.05 (1H, br d), 3.15–3.28 (1H, m), 3.35 (1H, d, J 16.3 Hz), 3.41 (1H, s), 3.74 (1H, d, J 16.2 Hz), 6.44 (2H, s), 6.80 (1H, s), 7.26–7.29 (7H, m), 7.87 (1H, s); MS (ES$^+$) m/z 415 (M+H, 100%).

EXAMPLE 17

(3RS,5RS,6SR)-3-(3,5-Bis(trifluoromethyl))phenyl-6-phenyl-7-azaspiro[4,5]decan-1-one This compound was prepared by the reaction of the enone of Description 8 and 3,5-bis(trifluoromethyl)bromobenzene according to the procedure described in Example 1. $^1$H NMR (400 MHz, CDCl$_3$) δ 1.75–1.83 (2H, m), 1.92 (1H, dd, J 18.6, 12.3 Hz), 2.03 (1H, t, J 12.4 Hz), 2.10–2.25 (3H, m), 2.78 (1H, dd, J 18.5, 7.4 Hz), 3.12 (1H, br t, J 13.3 Hz), 3.45–3.55 (2H, m), 4.18 (1H, s), 7.25–7.31 (5H, m), 7.37–7.38 (2H, m), 7.69 (1H, s); MS (ES$^+$) m/z 442 (M+H, 100%).

EXAMPLE 18

(3RS,5RS,6SR)-3-(3,5-Bis(trifluoromethyl))phenyl-6-phenyl-7-(1,2,4-triazol-3-yl)methyl-7-azaspiro[4,5]decan-1-one The compound of Example 17 was reacted according to the procedure described in Example 2 to afford the title compound. $^1$H NMR (400 MHz), CDCl$_3$) δ 1.55 (1H, dd, J 13.4, 4.0 Hz), 1.62 (1H, d, J 16.4 Hz), 1.81 (1H, dd, J 17.8, 12.8), 1.98–2.10 (2H, m), 2.19–2.34 (2H, m), 2.46 (1H, ddd, J 12.9, 12.9, 2.4 Hz), 2.69 (1H, ddd, J 17.8, 7.4, 1.6 Hz), 3.09 (1H, d, J 11.2 Hz), 3.35–3.46 (3H, m), 3.78 (1H, d, J 16.3 Hz), 7.14–7.38 (8H, m), 7.67 (1H, s), 7.90 (1H, s); MS (ES$^+$) m/z 523 (M+H, 100%).

EXAMPLE 19

(3SR,5RS,6SR)-3-(2-Difluoromethoxy-5-trifluoromethoxy)phenyl-6-phenyl-7-azaspiro[4,5] decan-1-one This compound was prepared by alkylation of the compound of Description 13 following the procedure of Description 19 and subsequent deprotection according to the procedure of Example Ib. $^1$H NMR (400 MHz, CDCl$_3$) δ 1.60 (1H, br d), 1.67 (1H, br ddd), 1.93 (1H, br d), 2.18–2.42 (6H, m), 2.80 (1H, ddd, J 13.0, 13.0, 3.3 Hz), 3.67 (1H, dd, J 12.8, 4.6 Hz), 3.66 (1H, s), 6.26 (1H, t, J 73.2 Hz), 6.95 (1H, s), 7.02 (2H, s), 7.26–7.36 (5H, m); MS (ES$^+$) m/z 456 (M+H, 100%).

EXAMPLE 20

(3SR,5RS,6SR)-3-(2-Difluoromethoxy-5-trifluoromethoxy)phenyl-6-phenyl-7-(1,2,4-triazol-3-yl)methyl-7-azaspiro[4,5]decan-1-one The compound of Example 19 was reacted according to the procedure described in Example 2 to afford the title compound. $^1$H NMR (400 MHz), CDCl$_3$) δ 1.23–1.28 (1H, m), 1.54–1.73 (3H, m), 1.93 (1H, d, J 13.4 Hz), 1.97–2.07 (1H, m), 2.27–2.51 (4H, m), 3.05 (1H, d, J 8.3 Hz), 3.34 (1H, d, J 16.3), 3.43 (1H, s), 3.78 (1H, d, J 16.4 Hz), 6.27 (1H, t, J 73.2 Hz), 6.93 (1H, d, J 2.2 Hz), 6.99–7.04 (2H, m), 7.26–7.31 (5H, m), 7.90 (1H, s); MS (ES$^+$) m/z 537 (M+H, 100%).

EXAMPLE 21

(3RS,5RS,6SR)-3-(2-Difluoromethoxy-5-(5-(trifluoromethyl)tetrazolyl))phenyl-6-phenyl-7-azaspiro[4,5]decan-1-one The compound of Description 19 was reacted according to the procedure described in Example Ib to afford the title compound. $^1$H NMR (360 MHz, CDCl$_3$) δ 1.56–1.68 (2H, m), 1.83 (1H, dd, J 17.9, 12.6 Hz), 1.96 (1H, ddd, J 12.9, 6.9, 2.0 Hz), 2.03–2.17 (2H, m), 2.24–2.30 (1H, m), 2.67 (1H, ddd, J 17.9, 7.5, 2.0 Hz), 2.80 (1H, ddd, 12.9, 12.9, 3.0 Hz), 3.36 (1H, dd, J 13.0, 4.1 Hz), 3.65 (1H, s), 3.68–3.77 (1H, m), 6.47 (1H, t, J 72.0 Hz), 6.77 (1H, d, J 2.4 Hz), 7.13–7.35 (7H, m); MS (ES$^+$) m/z 508 (M+H)

EXAMPLE 22

(3SR,5RS,6SR)-3-(2-Difluoromethoxy-5-(5-trifluoromethyl)tetrazolyl)phenyl-6-phenyl-7-azaspiro[4,5]decan-1-one The compound of Description 20 was reacted according to the procedure described in Example Ib to afford the title compound. $^1$H NMR (360 MHz, CDCl$_3$) δ 1.52 (1H, d, J 12.5 Hz), 1.61–1.71 (2H, m), 1.91 (1H, d, J 13.6 Hz), 2.42–2.47 (1H, m), 2.75 (1H, ddd, J 12.8, 12.8, 3.0 Hz), 3.36 (1H, dd, J 12.7, 4.5 Hz), 3.6 (1H, s), 6.42 (1H, t, J 72.4 Hz) 7.22 (1H, d, J 8.7 Hz), 7.25 (1H, dd, J 8.7, 2.7 Hz), 7.28–7.38 (6H, m); MS (ES$^+$) m/z 508 (M+H).

EXAMPLE 23

(3RS,5RS,6SR)-3-(2,6-dimethyl)phenyl-6-phenyl-7-azaspiro[4,5]decan-1-one

This compound was prepared by the reaction of the enone of Description 8 and 2,6-dimethylbromobenzene according to the procedure described in Example 1. $^1$H NMR (400 MHz, CDCl$_3$) δ 1.47 (1H, m), 1.61 (1H, ddd, J 13.6, 13.6, 4.3 Hz), 1.94–2.10 (9H, m), 2.12–2.20 (1H, m), 2.30–2.44 (1H, m), 2.48–2.90 (3H, m), 3.30 (1H, m), 3.59 (1H, s), 6.80–6.90 (3H, m), 7.26–7.31 (5H, m); MS (ES$^+$) m/z 334 (M+H, 100%).

EXAMPLE 24

(3RS,5RS,6SR)-3-Bis(trifluoromethyl)phenyl-7-(4-N,N-dimethylaminomethyl-1,2,3-triazol-5-yl)methyl-6-phenyl-7-azaspiro[4,5]decan-1-one (a) (3RS,5RS,6SR)-3-(3,5-Bis(trifluoromethyl))phenyl-7-(4-chlorobut-2-yn)yl-6-phenyl-7-azaspiro[4,5]decan-1-one The compound of Example 17 (0.2 g, 0.45 mmol) was dissolved in N,N-dimethylformamide and added to a mixture of potassium carbonate (0.186 g, 1.35 mmol) and 1,4-dichloro-2-butyne (0.126 ml, 1.26 mmol) in N,N-dimethylformamide (1.25 ml). The reaction was stirred at 60° C. for 3 hours under an atmosphere of nitrogen. Further 1,4-dichloro-2-butyne (0.09 ml, 0.9 mmol) and potassium carbonate (0.124 g, 0.9 mmol) were added and the mixture stirred for 1 hour. The reaction was diluted with water and the product was extracted into ethyl acetate. The combined organic extracts were washed with water, brine, dried (magnesium sulfate) and evaporated to afford a yellow oil. This was purified on silica, eluting with 15% ethyl acetate in hexane, increasing to 20% ethyl acetate in hexane, to afford the title compound as a yellow oil (100 mg). $^1$H NMR (400 MHz, CDCl$_3$) δ 1.49 (1H, td, J 13.6, 3.8 Hz), 1.63–1.76 (2H, m), 2.00–2.04 (1H, m), 2.14 (2H, t, J 12.8 Hz), 2.35 (1H, qt, J 13.2, 6.6 Hz), 2.58–2.71 (2H, m), 3.10 (1H, d, J 11.2 Hz), 3.28–3.39 (4H, m), 4.17 (2H, s), 7.23 (2H, s), 7.35 (5H, s), 7.67 (1H, s); MS (ES$^+$) m/z 528 (M+1).

(b) (3RS,5RS,6SR)-7-(4-Azido-2-butyn)yl-3-(3,5-bis(trifluoromethyl))phenyl-6-phenyl-7-azaspiro[4,5]decan-1-one The product of a) above (100 mg, 0.19 mmol) was dissolved in N,N-dimethylformamide (0.5 ml) and sodium azide (14 mg, 0.21 mmol) was added. The reaction was stirred at room temperature under an atmosphere of nitrogen for 16 hours. The reaction was diluted with water and the product extracted into ethyl acetate. The combined organic extracts were washed with water, brine, dried (magnesium sulfate) and evaporated to afford a yellow oil (101 mg). Signals: $^1$H NMR (360 MHz, CDCl$_3$) δ 1.42–1.55 (1H, m), 1.63–1.67 (1H,m), 1.71 (1H, d, J 4.6 Hz), 2.01 (1H, td, J 5.9, 2.0 Hz), 2.11–2.18 (2H, m), 2.37 (1H, qt, J 13.1, 4.0 Hz), 2.60 (1H, ddd, J 17.5, 7.2, 1.9 Hz), 2.71 (1H, td, J 12.7, 2.8 Hz), 3.08 (1H, d, J 11.4 Hz), 3.29–3.44 (4H, m), 3.95 (2H, s), 7.23 (2H, s), 7.35 (5H, s), 7.67 (1H, s); MS (ES$^+$) m/z 535.

(c) (3RS,5RS,6SR)-3-Bis(trifluoromethyl)phenyl-7-(4-N,N-dimethylaminomethyl-1,2,3-triazol-5-yl)methyl-6-phenyl-7-azaspiro[4,5]decan-1-one The azide described in b) above (100 mg, 0.19 mmol) was dissolved in dioxane and dimethylamine (excess) was added. The reaction vessel was sealed and the mixture stirred at 80° C. for 3 hours. The reaction was concentrated in vacuo to leave a yellow oil. This was purified on alumina, eluting in 50% ethyl acetate in hexane, gradually increasing to 100% ethyl acetate, then further elution with 1% methanol in ethyl acetate. It was further necessary to increase the polarity of the solvent to 100% methanol and finally eluting with 10% water in methanol to ensure complete elution of the product. The resultant title compound was a colourless oil (55 mg). The mono hydrogen chloride salt was made by dissolving the free base in ethyl acetate and adding a 1M solution of hydrogen chloride in ether (0.095 ml, 0.95 mmol). The salt was recrystallised from ethyl acetate and methanol to afford the title compound as a white solid. $^1$H NMR (500 MHz, Pyridine, d5) δ 1.43–1.49 (2H, m), 1.97 (1H, dd, J 17.5, 12.8 Hz), 2.06–2.28 (5H, m), 2.71 (1H, dd, J 17.5, 6.8 Hz), 2.95 (6H, s), 3.20 (1H, d, J 11.0 Hz), 3.27 (1H, s), 3.43–3.5 (2H, m), 3.90 (1H, d, J 13.9 Hz), 4.57 (1H, d, J 14.1 Hz), 4.62 (1H, d, J 14.0 Hz), 7.20 (1H, s), 7.31–7.34 (2H, m), 7.50 (4H, s), 8.72 (1H, s); MS (ES$^+$) m/z 580 (M+1).

What is claimed is:

1. A compound of the formula (I):

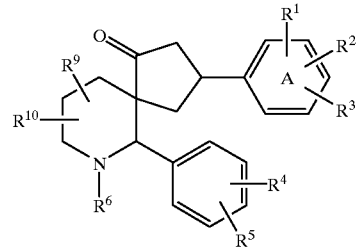

(I)

wherein $R^1$ represents hydroxy, $C_{1-6}$alkyl, fluoro$C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $R^1$ represents hydroxy, $C_{1-6}$alkyl, fluoro$C_{1-6}$alkyl, $C_{2-6}$alkenyl, $C_{2-6}$alkenyloxy, $C_{3-7}$cycloalkoxy, $C_{3-7}$cycloalkyl$C_{1-4}$alkoxy, phenoxy, cyano, halogen, $NR^aR^b$, $SR^a$, $SOR^a$, $SO_2R^a$, $OSO_2R^a$, $NR^aCOR^{14}$, $COR^a$, $CO_2R^a$ or $CONR^aR^b$ where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen and sulphur, which ring is optionally substituted by a group selected from $C_{1-4}$alkyl, $CF_3$, =O or =S;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{14}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

or $R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_r NR^aR^b$, —$(CH_2)_r NR^a COR^b$, —$(CH_2)_r CONR^aR^b$, or $CH_2C(O)R^a$, where $R^a$ and $R^b$ are as previously defined and r is zero, 1 or 2;

$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $CF_3$ or $C_{1-6}$alkoxy substituted by $C_{1-4}$alkoxy;

43

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}alkylR^{12}$, $CONR^{13}C_{2-6}alkenyl$, $CONR^{13}C_{2-6}alkynyl$, $COCONR^aR^b$, $CONR^a(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula —$CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where
Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^9$ and $R^{10}$ each independently represent hydrogen, halogen, $C_{1-6}$alkyl, $CH_2OR^e$, oxo, $CO_2R^a$ or $CONR^aR^b$ where $R^a$ and $R^b$ are as previously defined and $R^e$ represents hydrogen, $C_{1-6}$alkyl or phenyl;

$R^{12}$ represents $OR^a$, $CONR^aR^b$ or heteroaryl;

$R^{13}$ represents hydrogen or $C_{1-6}$alkyl; and $R^{14}$ represents $C_{1-6}$alkyl, $C_{1-6}$alkoxy, fluoro$C_{1-6}$alkyl or phenyl;

or a pharmaceutically acceptable salt thereof.

2. A compound as claimed in claim 1 wherein ring A represents a 2,5-disubstituted phenyl ring or a 3,5-disubstituted phenyl ring.

3. A compound as claimed in claim 1 wherein $R^1$ is hydroxy, $C_{1-6}$alkyl, fluoro$C_{1-6}$alkyl, $C_{2-6}$alkenyl, $C_{1-6}$alkoxy, fluoro$C_{1-6}$alkoxy, $C_{2-6}$alkenyloxy, $C_{3-7}$cycloalkoxy, $C_{3-7}$cycloalkyl$C_{1-4}$alkoxy, cyano, $NR^aR^b$, $SR^a$, $OSO_2R^a$, or $R^1$ together with the group $R^2$ form a 5-membered saturated ring containing one oxygen atom.

4. A compound as claimed in claim 1 wherein $R^3$ is hydrogen, halogen, fluoro$C_{1-6}$alkyl, fluoro$C_{1-6}$alkoxy, cyano, $NR^aR^b$, $NR^aCOR^{14}$ or a 5-membered aromatic heterocyclic group as defined in claim 1.

5. A compound as claimed in claim 1 wherein $R^5$ is a hydrogen atom.

44

6. A compound as claimed in claim 1 wherein $R^9$ and $R^{10}$ are both hydrogen atoms.

7. A compound of the formula (Ia):

(Ia)

wherein
$R^2$, $R^4$ and $R^6$ are as defined in claim 1;
$R^{1a}$ is $C_{1-4}$alkoxy, fluoro$C_{1-4}$alkoxy, $C_{3-5}$cycloalkoxy or $C_{3-5}$cycloalkoxy$C_{1-2}$alkyl; and
$R^{3a}$ is fluoro$C_{1-4}$alkoxy;
or a pharmaceutically acceptable salt thereof.

8. A compound as claimed in claim 1 wherein $R^2$ is a hydrogen, fluorine or chlorine atom.

9. A compound of the formula (Ib):

(Ib)

wherein
$R^4$ and $R^6$ are as defined in claim 1;
$R^{1b}$ is $C_{1-4}$alkyl, or fluoro$C_{1-4}$alkyl; and
$R^{3b}$ is $C_{1-4}$alkyl or fluoro$C_{1-4}$alkyl;
or a pharmaceutically acceptable salt thereof.

10. A compound as claimed in claim 1 wherein $R^4$ is a hydrogen atom or a fluorine atom.

11. A compound as claimed in claim 1 wherein $R^6$ is a hydrogen atom.

12. A compound as claimed in claim 1 wherein $R^6$ is a $C_{1-6}$alkyl group substituted by a 5-membered heterocyclic ring containing 2 or 3 nitrogen atoms as defined in claim 1.

13. A compound selected from:

(3RS,5RS,6SR)-3-(2-methoxy-5-trifluoromethoxy)phenyl-6-phenyl-7H-azaspiro4,5]decan-1-one;

(3RS,5RS,6SR)-3-(2-methoxy-5-trifluoromethoxy)phenyl-6-phenyl-7-(1,2,4-triazol-3-yl)methyl-7-azaspiro[4,5]decan-1-one;

(3RS,5RS,6SR)-3-(2-cyclopropoxy-5-trifluoromethoxy)phenyl-6-phenyl-7-azaspiro[4,5]decan-1-one;

(3SR,5RS,6SR)-3-(2-cyclopropoxy-5-trifluoromethoxy)phenyl-6-phenyl-7-azaspiro[4,5]decan-1-one;

(3RS,5RS,6SR)-3-(2-cyclopropoxyoxy-5-trifluoromethoxy)phenyl-6-phenyl-7-(1,2,4-triazol-3-yl)methyl-7-azaspiro[4,5]decan-1-one;

(3SR,5RS,6SR)-3-(2-methoxy-5-trifluoromethoxy)phenyl-6-phenyl-7H-azaspiro[4,5]decan-1-one;

(3RS,5RS,6SR)-3-(2-isopropoxy-5-trifluoromethoxy)phenyl-6-phenyl-7-azaspiro[4,5]decan-1-one;

(3RS,5RS,6SR)-3-(2-isopropoxy-5-trifluoromethoxy)phenyl-6-phenyl-7-(1,2,4-triazol-3-yl)methyl-7-azaspiro[4,5]decan-1-one;

(3RS,5RS,6SR)-3-(2-hydroxy-5-trifluoromethoxy)phenyl-6-phenyl-7-azaspiro[4,5,]decan-1-one;

(3RS,5RS,6SR)-3-(2-cyclopropylmethyloxy-5-trifluoromethoxy)phenyl-6-phenyl-7-azaspiro[4,5,]decan-1-one;

(3RS,5RS,6SR)-3-(2-difluoromethoxy-5-trifluoromethoxy)phenyl-6-phenyl-7-azaspiro[4,5]decan-1-one;

(3RS,5RS,6SR)-3-(2-difluoromethoxy-5-trifluoromethoxy)phenyl-6-phenyl-7-(1,2,4-triazol-3-yl)methyl-7-azaspiro[4,5]decan-1-one;

(3RS,5RS,6SR)-6-phenyl-3-(2-(2,2,2-trifluoroethoxy-5-trifluoromethoxy)phenyl-7-azaspiro[4,5,]decan-1-one;

(3RS,5RS,6SR)-6-phenyl-7-(1,2,4-triazol-3-yl)methyl-3-(2-(2,2,2-trifluoroethoxy-5-trifluoromethoxy)phenyl-7-azaspiro[4,5]decan-1-one;

(3SR,5RS,6SR)-3-(3,5-dimethyl)phenyl-6-phenyl-7-azaspiro[4,5]decan-1-one;

(3SR,5RS,6SR)-3-(3,5-dimethyl)phenyl-6-phenyl-7-(1,2,4-triazol-3-yl)methyl-7-azaspiro[4,5]decan-1-one;

(3RS,5RS,6SR)-3-(3,5-bis(trifluoromethyl))phenyl-6-phenyl-7-azaspiro[4,5]decan-1-one;

(3RS,5RS,6SR)-3-(3,5-bis(trifluoromethyl))phenyl-6-phenyl-7-(1,2,4-triazol-3-yl)methyl-7-azaspiro[4,5]decan-1-one;

(3SR,5RS,6SR)-3-(2-difluoromethoxy-5-trifluoromethoxy)phenyl-6-phenyl-7-azaspiro[4,5]decan-1-one;

(3SR,5RS,6SR)-3-(2-difluoromethoxy-5-trifluoromethoxy)phenyl-6-phenyl-7-(1,2,4-triazol-3-yl)methyl-7-azaspiro[4,5]decan-1-one;

(3RS,5RS,6SR)-3-(2-difluoromethoxy-5-(5-(trifluoromethyl)tetrazolyl))phenyl-6-phenyl-7-azaspiro[4,5]decan-1-one;

(3SR,5RS,6SR)-3-(2-difluoromethoxy-5-(5-trifluoromethyl)tetrazolyl)phenyl-6-phenyl-7-azaspiro[4,5]decan-1-one;

(3RS,5RS,6SR)-3-(2,6-dimethyl)phenyl-6-phenyl-7-azaspiro[4,5]decan-1-one;

or a pharmaceutically acceptable salt thereof.

14. A pharmaceutical composition comprising a compound as claimed in claim 1, together with at least one pharmaceutically acceptable carrier or excipient.

15. A method for the treatment or prevention of physiological disorders associated with an excess of tachykinins, which method comprises administration to a patient in need thereof of a tachykinin reducing amount of a compound according to claim 1.

16. A method according to claim 15 for the treatment or prevention of pain or inflammation, migraine, emesis, postherpetic neuralgia, depression or anxiety.

17. A process for the preparation of a compound as claimed in claim 1 which comprises:

(A) reaction of a compound of formula (II)

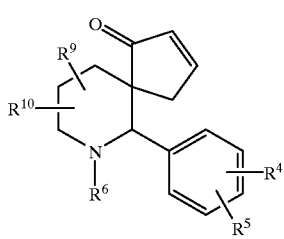

(II)

wherein $R^4$, $R^5$, $R^6$, $R^9$ and $R^{10}$ are as defined in claim 1, with a Grignard reagent of the formula (III)

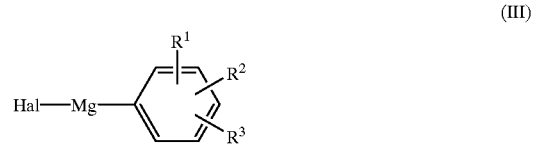

(III)

wherein $R^1$, $R^2$ and $R^3$ are as defined in claim 1 and Hal is a halogen atom; or (B) reduction of a compound of formula (IV):

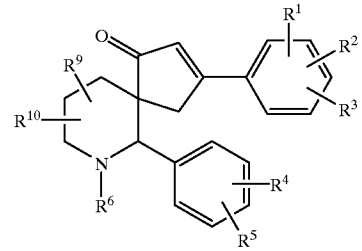

(IV)

wherein $R^1$, $R^2$, $R^3$, $R^4$, $R^5$, $R^6$, $R^9$ and $R^{10}$ are as defined in claim 1; or (C) interconversion of a corresponding compound of formula (I) in which $R^6$ is H, i.e. a compound of formula (V)

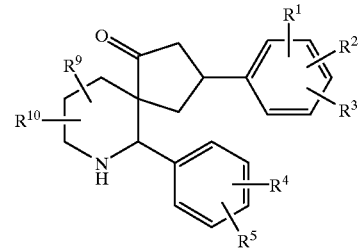

(V)

by reaction with a compound of formula (VI):

(VI)

where $R^{6a}$ is a group of the formula $R^6$ as defined in relation to claim 1 (other than H) or a precursor therefor and LG is a leaving group; and, if $R^{6a}$ is a precursor group, converting it to a group R ; or (D) where $R^1$ is $C_{1-6}$alkoxy, fluoro$C_{1-6}$alkoxy, $C_{2-6}$alkenoxy, $C_{3-7}$cycloalkoxy, or $C_{3-7}$cycloalkyl$C_{1-4}$alkoxy, interconversion of a compound of formula (I) wherein $R^1$ is hydroxy, i.e. a compound of formula (VII)

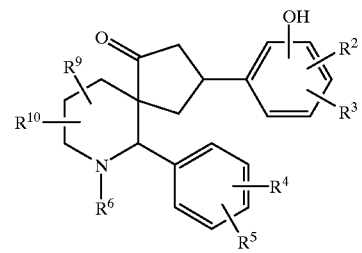

(VII)

by reaction with an appropriate alkyl-, fluoroalkyl-, alkenyl-, cycloalkyl-, or cycloalkylalkyl-halide, in the presence of a base; or (E) reaction of a compound of formula (II) and a compound of formula (IV), where Hal in the compound of formula (IV) is chlorine, bromine or iodine, by a reductive Heck reaction using a palladium catalyst with tri-o-tolylphosphine, dimethylformamide and tributylamine; or tetrabutylammonium chloride and dimethylformamide, and a reducing agent; or (F) where $R^1$ is cyclopropoxy, reaction of a compound of formula (VIII):

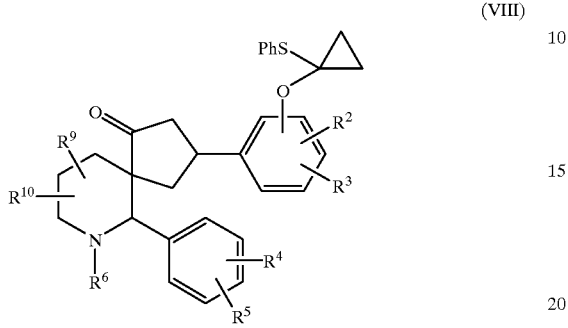

(VIII)

with lithium naphthalenide in tetrahydrofuran; or (G) where $R^6$ is 1,2,4-triazol-3-ylmethyl, reaction of a compound of formula (V) and N-formyl-2-chloroacetamidhyrazone in the presence of a base; or (H) where $R^6$ is a 1,2,3-triazol-4-ylmethyl group substituted by $CH_2NR^7R^8$, reaction of a compound of formula (IX)

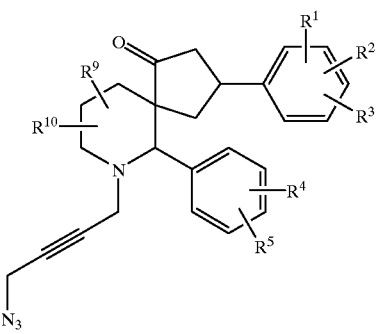

(IX)

with an amine of formula $NHR^7R^8$, in a solvent at elevated temperature;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *